(12) United States Patent
Shu

(10) Patent No.: US 11,485,726 B2
(45) Date of Patent: Nov. 1, 2022

(54) COMPOUND FOR INHIBITING AND DEGRADING TYROSINE PROTEIN KINASE ALK

(71) Applicant: SHANGHAI MEIZER PHARMACEUTICALS CO., LTD., Shanghai (CN)

(72) Inventor: Yongzhi Shu, Shanghai (CN)

(73) Assignee: SHANGHAI MEIZER PHARMACEUTICALS CO., LTD., Shanghai (CN)

( * ) Notice: Subject to any disclaimer, the term of this patent is extended or adjusted under 35 U.S.C. 154(b) by 0 days.

(21) Appl. No.: 16/808,333

(22) Filed: Mar. 3, 2020

(65) Prior Publication Data

US 2020/0199106 A1 Jun. 25, 2020

Related U.S. Application Data

(63) Continuation of application No. PCT/CN2018/103709, filed on Sep. 2, 2018.

(30) Foreign Application Priority Data

Sep. 3, 2017 (CN) .......................... 201710783067.0

(51) Int. Cl.
*C07D 401/14* (2006.01)
*A61P 35/00* (2006.01)

(52) U.S. Cl.
CPC ............ *C07D 401/14* (2013.01); *A61P 35/00* (2018.01)

(58) Field of Classification Search
CPC ............................... C07D 401/14; A61P 35/00
See application file for complete search history.

(56) References Cited

U.S. PATENT DOCUMENTS

2020/0199132 A1* 6/2020 Shu .......................... A61P 17/06
2020/0216450 A1* 7/2020 Shu .......................... A61K 31/54

FOREIGN PATENT DOCUMENTS

| CN | 106336382 A | | 1/2017 |
|---|---|---|---|
| WO | 2017204445 | * | 11/2017 |
| WO | 2017204445 A2 | | 11/2017 |

OTHER PUBLICATIONS

International Search Report and Written Opinion (in Chinese and English) issued in PCT/CN2018/103709, dated Nov. 28, 2018, 17 pages provided.
Zhang et al., "Proteolysis Targeting Chimeras (PROTACs) of Anaplastic Lymphoma Kinase (ALK)", European Journal of Medicinal Chemistry, vol. 151, Mar. 23, 2018; 36 pages provided.

* cited by examiner

*Primary Examiner* — Paul V Ward
(74) *Attorney, Agent, or Firm* — Hamre, Schumann, Mueller & Larson, P.C.

(57) ABSTRACT

Provided is a compound for inhibiting and degrading anaplastic lymphoma kinase ALK. Specifically provided is a compound as represented by the following formula I, wherein the definition of each group is as stated in the description. The compound has excellent anaplastic lymphoma kinase (ALK) inhibitory activity, and can be used for preparing drugs for treatment of ALK activity-related diseases.

9 Claims, No Drawings

COMPOUND FOR INHIBITING AND DEGRADING TYROSINE PROTEIN KINASE ALK

TECHNICAL FIELD

The present invention belongs to the field of medicine, and particularly relates to a class of compounds inhibiting and degrading tyrosine protein kinase ALK, the preparation thereof and the application thereof.

BACKGROUND

Anaplastic lymphoma kinase (ALK) is a receptor-type protein tyrosine phosphokinase. It can accept extracellular signals and regulate cell growth, differentiation, survival and transformation. Structurally, ALK includes an extracellular ligand-binding region, a transmembrane region, and an intracellular domain.

Initially, ALK was discovered as an activated fusion oncogene in anaplastic large cell lymphoma and in subsequent studies fusion forms of ALK have been found in a variety of cancers, including systemic tissue dysplasia, inflammatory myofibroblastoma, non-small cell lung cancer, etc. The ALK mutation and its abnormal activities in a variety of cancers have made ALK a drug target for treating ALK-positive cancers.

The forms of ALK mutations have phenomenons such as overexpression, formation of fusion genes with other genes, and point mutations. ALK gene fusion mutation is a common driver gene in non-small cell lung cancer (NSCLC). The percentage of ALK fusion mutations positive in Chinese non-small cell lung adenocarcinoma is 5.3%, and it has higher incidence in younger patients (younger than 60 years) with non-small cell lung adenocarcinoma and non-smokers. ALK-positive non-small cell lung cancer is considered as a molecular subtype, and the corresponding targeting drug is completely different from the EGFR molecular subtype. A number of drugs as an ALK inhibitor (eg, crizotinib, erlotinib, ceritinib) have been marketed for the treatment of non-small cell lung cancer.

Therefore, those skilled in the art are dedicated to developing compounds capable of inhibiting the tyrosine protein kinase ALK activity.

SUMMARY OF THE INVENTION

The object of the present invention is to provide a compound capable of inhibiting and degrading tyrosine protein kinase ALK, the preparation thereof and the application thereof.

In the first aspect of the present invention, there is provided a compound represented by the following formula I, or a pharmaceutically acceptable salt thereof:

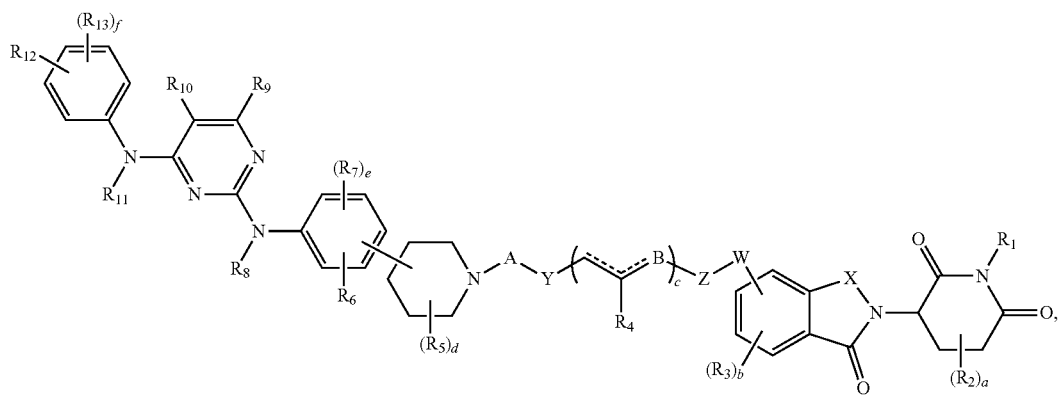

I wherein,
— refers to a single bond;
═ refers to a single or double bond;
A is missing or selected from $C(=O)$, $C(=O)X1$, $(CR_{35}R_{36})_kC(=O)X1$, $SOX1$, $SO_2X1$, $C_{1-8}$ hydrocarbyl group with or without substituent(s), $C_{1-8}$ cyclic hydrocarbyl group with or without substituent(s), and $C_{1-8}$ heterocyclic hydrocarbyl group with or without substituent(s); wherein X1 is missing or selected from $(CR_{35}R_{36})_kO$, $(CR_{35}R_{36})_kS$ and $NR_{14}$; wherein $R_{35}$, $R_{36}$, $R_{14}$ is each independently selected from H, $C_{1-8}$ hydrocarbyl group with or without substituent(s), $C_{1-8}$ cyclic hydrocarbyl group with or without substituent(s) and $C_{1-8}$ heterocyclic hydrocarbyl group with or without substituent(s); k is an integer between 0 and 3;

W is missing or selected from O, $NR_{17}$, —$X2C(=O)X3$, and —$X2S(=O)_gX3$; wherein $R_{17}$ is H, $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s); wherein X2, X3 is each independently missing or selected from O, S, and $NR_{18}$; wherein g is an integer between 0 and 2; wherein $R_{18}$ is H, $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s);

Y is $(CR_{22}R_{23})_h$, $CHX4(CR_{22}R_{23})_h$, $CX4=CH(CR_{22}R_{23})_h$, or $(CR_{22}R_{23})_h$; wherein h is an integer between 0 and 30; wherein $R_{22}$, $R_{23}$ is each independently selected from H, cyano, hydroxyl, amino, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s), and $C_{1-8}$ hydrocarbyloxy group with or without substituent(s); wherein X4 is H, halogen, cyano, nitro, hydroxyl, $C_{1-8}$ hydrocarbyloxy group with or without substituent(s), $C_{1-8}$ hydrocarbyloxycarbonyl group with or without substituent(s), $C_{1-8}$ amino group with or without substituent(s), $C_{1-8}$ ester group with or without substituent(s), $C_{1-8}$ aminocarbonyl group with or without substituent(s), $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s);

Z is $(CR_{24}R_{25})_i$, $CHX5(CR_{24}R_{25})_i$, $CX5=CH(CR_{24}R_{25})_i$ or $C≡C(CR_{24}R_{25})_i$; wherein i is an integer between 0 and 30; wherein $R_{24}$, $R_{25}$ is each independently selected from H, cyano, hydroxyl, amino, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s), and $C_{1-8}$ hydrocarbyloxy group with or without substituent(s); wherein X5 is H, halogen, cyano, nitro, hydroxyl, $C_{1-8}$ hydrocarbyloxy group with or without substituent(s), $C_{1-8}$ hydrocarbyloxycarbonyl group with or without substituent(s), $C_{1-8}$ amino group with or without substituent(s), $C_{1-8}$ ester group with or without substituent(s), $C_{1-8}$ aminocarbonyl group with or without substituent(s), $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s);

B is missing or selected from O, C=O, S, $NR_{15}$, $-NR_{15}C(=O)-$, $-C(=O)NR_{15}-$, $-C(=O)O-$, $OC(=O)O-$, $-NR_{15}C(=O)O-$, $-OC(=O)NR_{15}-$, $-NR_{15}C(=O)NR_{16}-$, $C_{1-12}$ hydrocarbyl group with or without substituent(s), $C_{1-12}$ cyclic hydrocarbyl group with or without substituent(s), and $C_{1-12}$ heterocyclic hydrocarbyl group with or without substituent(s); wherein $R_{15}$, $R_{16}$ is each independently selected from H, $C_{1-8}$ hydrocarbyl group with or without substituent(s), $C_{1-8}$ cyclic hydrocarbyl group with or without substituent(s), and $C_{1-8}$ heterocyclic hydrocarbyl group with or without substituent(s);

X is selected from $CR_{19}R_{20}$, $C(=O)$, $S(=O)$, $SO_2$, and $NR_{21}$; wherein $R_{19}$, $R_{20}$ is each independently selected from H, cyano, hydroxyl, amino, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s), and $C_{1-8}$ hydrocarbyloxy group with or without substituent(s); wherein $R_{21}$ is selected from H, $C_{1-8}$ hydrocarbyl group with or without substituent(s), $C_{1-8}$ cyclic hydrocarbyl group with or without substituent(s), and $C_{1-8}$ heterocyclic hydrocarbyl group with or without substituent(s);

$R_1$, $R_8$, $R_{11}$ is each independently selected from H, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s) and $C_{1-6}$ acyl group with or without substituent(s);

$R_2$, $R_5$ is each independently selected from hydrogen, $OR_{26}$, $NR_{27}R_{28}$, cyano, halogen, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s), $C_{1-6}$ acyl group with or without substituent(s) and $C_{1-6}$ amido group with or without substituent(s); wherein $R_{26}$, $R_{27}$, $R_{28}$ is each independently selected from H, $C_{1-8}$ hydrocarbyl group with or without substituent(s), $C_{1-8}$ cyclic hydrocarbyl group with or without substituent(s), and $C_{1-8}$ heterocyclic hydrocarbyl group with or without substituent(s);

$R_3$, $R_6$, $R_7$, $R_9$, $R_{10}$, $R_{12}$, $R_{13}$ is each independently selected from H, $OR_{29}$, $NR_{30}R_{31}$, cyano, halogen, nitro, $C_{1-8}$ hydrocarbyl group with or without substituent(s), cyclic hydrocarbyl group with or without substituent(s), heterocyclic hydrocarbyl group with or without substituent(s), X6S$(=O)_jR_{32}$, and $X6C(=O)R_{33}$; wherein j is an integer between 0 to 2; wherein $R_{29}$, $R_{30}$, $R_{31}$, $R_{32}$, $R_{33}$ is each independently selected from H, $C_{1-8}$ hydrocarbyl group with or without substituent(s), $C_{1-8}$ cyclic hydrocarbyl group with or without substituent(s) and $C_{1-8}$ heterocyclic hydrocarbyl group with or without substituent(s); wherein X6 is missing or selected from O, S, and $NR_{34}$; wherein $R_{34}$ is H, $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s);

$R_4$ is selected from H, cyano, carboxyl, $C_{1-8}$ hydrocarbyl group with or without substituent(s), and $C_{1-8}$ hydrocarbyloxycarbonyl group with or without substituent(s);

a is an integer between 0 and 5 (such as 1, 2, 3, 4, 5);

b is an integer between 0 and 3 (such as 1, 2, 3);

c is an integer between 0 and 30 (such as 1, 2, 3, 4, 5, 6, 7, 8, 9);

d is an integer between 0 and 9 (such as 1, 2, 3, 4, 5, 6, 7, 8, 9);

e is an integer between 0 and 3 (such as 1, 2, 3);

f is an integer between 0 and 4 (such as 1, 2, 3, 4).

In another preferred example, A is missing; W is —X2C(=O)X3, wherein X3 is $NR^{18}$ and X2 is missing, or X2 is $NR_{18}$ and X3 is missing; Y is $(CR_{22}R_{23})_h$, wherein $R_{22}$, $R_{23}$ is each independently selected from H, hydroxyl, and $C_{1-4}$ hydrocarbyl group with or without substituent(s), h is an integer between 1 and 6; Z is $(CR_{24}R_{25})_i$, wherein $R_{24}$, $R_{25}$ is each independently selected from H, hydroxyl, and $C_{1-4}$ hydrocarbyl group with or without substituent(s), i is an integer between 1 and 6; c is 0.

In another preferred example, A is missing; W is missing or O; Y is $(CR_{22}R_{23})_h$, wherein $R_{22}$, $R_{23}$ is each independently selected from H, hydroxyl, and $C_{1-4}$ hydrocarbyl group with or without substituent(s), h is an integer between 0 and 3; B is O; Z is $(CR_{24}R_{25})_i$, wherein $R_{24}$, $R_{25}$ is each independently selected from H, hydroxyl, and $C_{1-4}$ hydrocarbyl group with or without substituent(s), i is an integer between 0 and 3; c is an integer between 1 and 6.

In another preferred example, A is $C(=O)X1$; wherein X1 is missing or selected from $(CR_{35}R_{36})_kO$ and $(CR_{35}R_{36})_k S$, wherein k is an integer between 0 and 2; $R_{35}$, $R_{36}$ is each independently H, or $C_{1-4}$ alkyl; W is $NR_{17}$, wherein $R_{17}$ is H, or $C_{1-4}$ hydrocarbyl group with or without substituent(s); Y is $(CR_{22}R_{23})_h$, wherein $R_{24}$, $R_{25}$ is each independently selected from H, hydroxyl, and $C_{1-4}$ hydrocarbyl group with or without substituent(s), h is an integer between 0 and 3; Z is $(CR_{24}R_{25})_i$, wherein $R_{24}$, $R_{25}$ is each independently selected from H, hydroxyl, $C_{1-4}$ hydrocarbyl group with or without substituent(s), i is an integer between 0 and 3; B is 0; c is an integer between 1 and 4.

In another preferred example, A is $SO_2X1$; wherein X1 is missing or selected from O and S; W is O; Y is $(CR_{22}R_{23})_h$, wherein $R_{22}$, $R_{23}$ is each independently selected from H, hydroxyl, and $C_{1-4}$ hydrocarbyl group with or without substituent(s), h is an integer between 1 and 6; Z is $(CR_{24}R_{25})_i$, wherein $R_{24}$, $R_{25}$ is each independently selected from H, hydroxyl, and $C_{1-4}$ hydrocarbyl group with or without substituent(s), i is an integer between 0 and 3; c is 0.

In another preferred example, A is missing; W is $NR_{17}$; wherein $R_{17}$ is H, or $C_{1-4}$ hydrocarbyl group with or without substituent(s); Y is $(CR_{22}R_{23})_h$, wherein $R_n$, $R_{23}$ is each independently selected from II, hydroxyl, and $C_{1-4}$ hydrocarbyl group with or without substituent(s), h is an integer between 0 and 3; Z is $(CR_{24}R_{25})_h$, wherein $R_{24}$, $R_{25}$ is each independently selected from II, hydroxyl, and $C_{1-4}$ hydrocarbyl group with or without substituent(s), i is an integer between 0 and 4; B is O; c is an integer between 1 and 6.

In another preferred example, A is missing; W is missing; Y is $(CR_{22}R_{23})_{11}$, wherein $R_{22}$, $R_{23}$ is each independently selected from H, hydroxyl, and $C_{1-4}$ hydrocarbyl group with or without substituent(s), h is an integer between 0 and 3; Z is $(CR_{24}R_{25})_i$, wherein $R_{24}$, $R_{25}$ is each independently selected from FI, hydroxyl, and $C_{1-4}$ hydrocarbyl group with or without substituent(s), i is an integer between 0 and 3; B is O; c is an integer between 1 and 10.

In another preferred example, A is $(CH_2)_kC(=O)X1$; wherein X1 is missing or —NH—; k is an integer between 1 and 3.

In another preferred example, any of the substituents is selected from the group consisting of halogen, unsubstituted or halogenated C1-C6 alkyl, unsubstituted or halogenated C1-C6 alkoxy, unsubstituted or halogenated C2-C6 alkoxyalkyl, unsubstituted or halogenated C3-C8 cycloalkyl, unsubstituted or halogenated C2-C6 alkylcarbonyl, unsubstituted or halogenated C1-C6 alkylene-hydroxyl, unsubstituted or C1-C6 alkyl substituted amine.

In another preferred example, the structure of the compound is represented by formula I':

In another preferred example, in formula I, F, r, or I''', ═══ refers to a single bond.

In another preferred example, X is C(═O).

In another preferred example, $R_1$, $R_8$, $R_{11}$ is each independently selected from H and $C_{1-4}$ alkyl with or without substituent(s).

In another preferred example, $R_2$, $R_5$ is each independently selected from H and $C_{1-4}$ alkyl with or without substituent(s).

In another preferred example, $R_3$ is selected from H and $C_{1-4}$ alkyl with or without substituent(s).

In another preferred example, $R_6$ is selected from II, $C_{1-4}$ alkyl with or without substituent(s), and $OR_{29}$; wherein $R_{29}$ is selected from H and $C_{1-6}$ alkyl with or without substituent(s).

In another preferred example, $R_7$ is selected from H and $C_{1-4}$ alkyl with or without substituent(s).

In another preferred example, $R_9$ is selected from H and $C_{1-4}$ alkyl with or without substituent(s).

In another preferred example, $R_{10}$ is selected from halogen, cyano, nitro, and $C_{1-4}$ alkyl with or without substituent(s).

In another preferred example, $R_{12}$ is selected from hydrogen, halogen, cyano, nitro, and $X6S(=O)_jR_{32}$; wherein X6 is missing and $R_{32}$ is selected from H and $C_{1-6}$ alkyl with or without substituent(s).

In another preferred example, $R_4$ is selected from H, cyano and $C_{1-6}$ alkyl with or without substituent(s).

I'

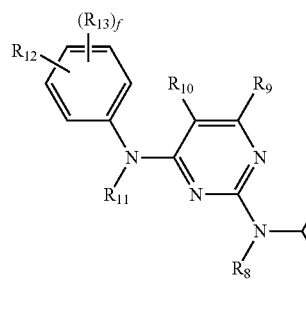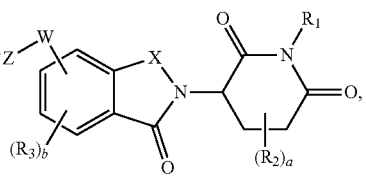

wherein, each group is defined as described above.

In another preferred example, the structure of the compound is represented by formula I":

I"

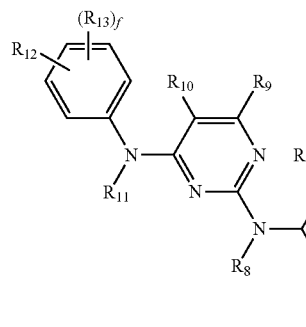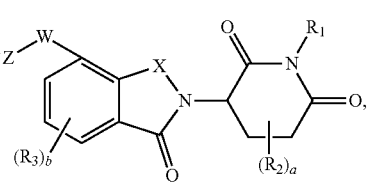

wherein, each group is defined as described above.

In another preferred example, $R_{12}$ is $X6S(\!\!=\!\!O)_jR_{32}$; wherein X6 is missing, j is 2 and $R_{32}$ is $C_{1-3}$ alkyl (preferably isopropyl) with or without substituent(s).

In the second aspect of the present invention, there is provided a pharmaceutical composition, which comprises the compound according to the first aspect or a pharmaceutically acceptable salt thereof, or a prodrug thereof, and a pharmaceutically acceptable carrier.

In another preferred example, the effective amount refers to a therapeutically effective amount or an inhibitory effective amount, preferably 0.01 to 99.99%.

In another preferred example, the pharmaceutical composition further comprises one or more other antitumor agents.

In another preferred example, the pharmaceutical composition is used to inhibit the activity of anaplastic lymphoma kinase (ALK).

In another preferred example, the pharmaceutical composition is used for treating diseases related to the activity or expression level of anaplastic lymphoma kinase (ALK).

In the third aspect of the present invention, there is provided a use of the compound according to the first aspect of the present invention for:

(a) preparation of drugs for the treatment of diseases related to the activity or expression level of anaplastic lymphoma kinase (ALK);

(b) preparation of anaplastic lymphoma kinase (ALK) targeted inhibitors or degradation agents;

(c) non-therapeutic inhibition or degradation of anaplastic lymphoma kinase (ALK) in vitro;

(d) non-therapeutic inhibition of tumor cell proliferation in vitro; and/or (e) treatment of diseases related to the activity or expression level of anaplastic lymphoma kinase (ALK).

In another preferred example, the disease includes a tumor, and preferably, the tumor includes non-small cell lung cancer, inflammatory myofibroblastoma, and the like.

In the forth aspect of the present invention, there is provided a method for preparing the compound of formula I according to the first aspect of the present invention, comprising the steps of:

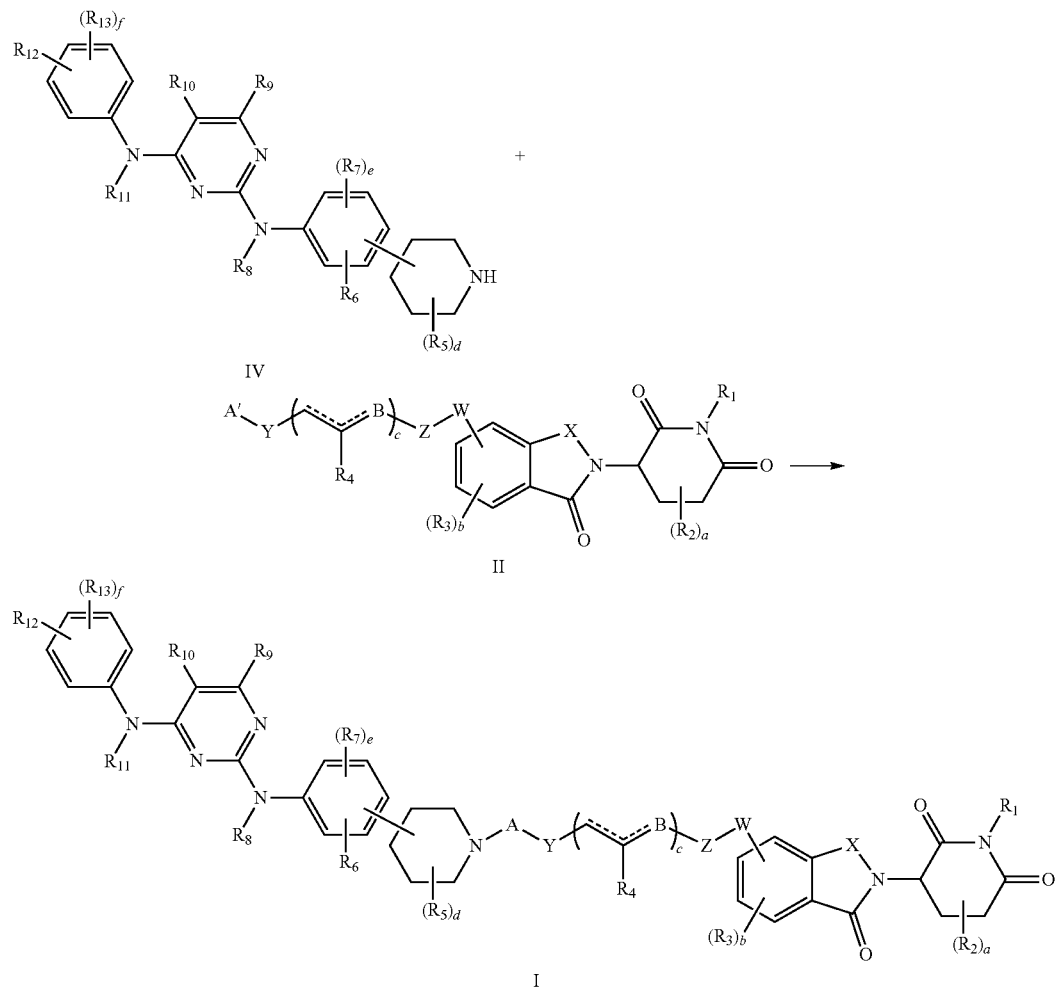

(a) reacting a compound of formula IV and a compound of formula II in an inert solvent to obtain a compound of formula I;

wherein, each group is defined as described above.

In another preferred example, the method further comprises the step of:

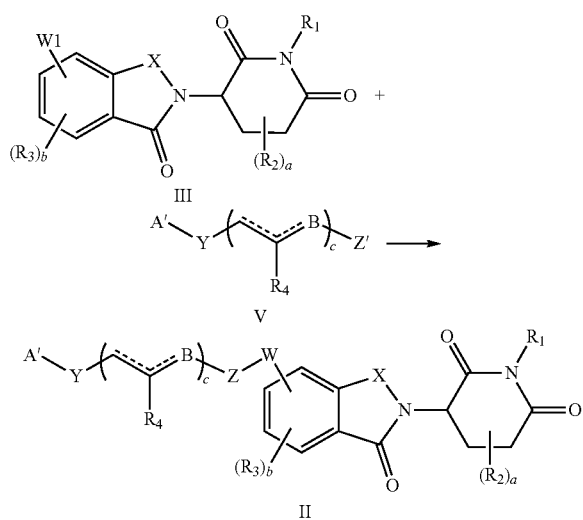

(a) reacting a compound of formula III and a compound of formula V in an inert solvent to obtain a compound of formula I.

In the fifth aspect of the present invention, there is provided a method for inhibiting or degrading anaplastic lymphoma kinase (ALK), comprising the step of administering an inhibitory effective amount of the compound of formula I according to the first aspect of the present invention or a pharmaceutically acceptable salt thereof to an inhibitory subject, or administering an inhibitory effective amount of the pharmaceutical composition according to the fourth aspect of the present invention to an inhibitory subject.

In another preferred example, the inhibition is non-therapeutic inhibition in vitro.

In another preferred example, when an inhibitory effective amount of the compound of formula I according to claim 1 or a pharmaceutically acceptable salt thereof is administered to an inhibitory subject, the inhibitory effective amount is 0.001-500 nmol/L, preferably 0.01-200 nmol/L.

In the sixth aspect of the present invention, there is provided a method for treating a disease related to the activity or expression level of anaplastic lymphoma kinase (ALK), comprising a step of: administering a therapeutically effective amount of the compound of formula I according to the first aspect of the present invention or the pharmaceutical composition according to the fourth aspect of the present invention to a subject in need of treatment.

In another preferred example, the subject is a mammal; preferably, the mammal is a human.

In another preferred example, the disease related to the activity or expression level of anaplastic lymphoma kinase (ALK) is a tumor, preferably the tumor is selected from the group consisting of non-small cell lung cancer.

In the seventh aspect of the present invention, there is provided a method for inhibiting tumor cells in vitro, comprising: administering an inhibitory effective amount of the compound of formula I according to the first aspect of the present invention or the pharmaceutical composition according to the second aspect of the present invention to an inhibitory subject.

It is to be understood that within the scope of the present invention, the various technical features of the present invention and the various technical features specifically described hereinafter (as in the embodiments) may be combined with each other to form a new or preferred technical solution. Due to space limitations, we will not repeat them here.

DETAILED DESCRIPTION OF THE INVENTION

After extensive and intensive research, the present inventors have prepared a class of compounds having the structure as shown in formula I and found that they have inhibitory and degradation activities to anaplastic lymphoma kinase (ALK). In addition, the compound has an inhibitory effect on anaplastic lymphoma kinase (ALK) at a very low concentration, and the inhibitory activity is quite excellent, so it can be used for the treatment of diseases related to the activity or expression level of anaplastic lymphoma kinase (ALK), such as tumors. The present invention has been completed on this basis.

The present invention discloses a new class of compounds and their use for inhibiting and degrading tyrosine protein kinase (ALK). These compounds can inhibit and degrade ALK and be used to treat non-small cell lung cancer.

Term

In the present invention, the term "$C_{1-8}$ hydrocarbyl group" refers to a functional group containing only two kinds of atoms of carbon and hydrogen, in which the number of carbon atoms is 1 to 8. A hydrocarbyl group can be regarded as a free radical left after the corresponding hydrocarbon loses one hydrogen atom, which may be an alkyl group, a cycloalkyl group, an alkenyl group, an alkynyl group, etc.; its structure may be linear, branched, or cyclic; and it may be aliphatic or aromatic. The term "$C_{1-6}$ alkyl" refers to a straight or branched alkyl group having 1 to 6 carbon atoms, such as methyl, ethyl, propyl, isopropyl, butyl, isobutyl, sec-butyl, tert-butyl, or similar groups.

The term "alkoxy" as used herein includes O-alkyl, in which "alkyl" is as defined above.

The term "halo" as used herein, unless otherwise indicated, includes fluoro, chloro, bromo or iodo.

The compound of the present invention may contain a double bond. When such double bond is contained, the compound of the present invention exists in cis form, trans form or mixtures thereof.

The halogens described herein include fluorine, chlorine, bromine and iodine.

Unless otherwise indicated, the alkyl and alkyl moieties of the alkoxy group described herein may be linear, branched, or cyclic.

In the present invention, the term "cyclic hydrocarbyl group" refers to a functional group containing two kinds of atoms of carbon and hydrogen, and includes cycloalkyl, cycloalkenyl (containing at least one carbon-carbon double bond), and aryl. They may be monocyclic, bicyclic or polycyclic. They may be Spiro rings or fused rings.

In the present invention, the term "heterocyclic hydrocarbyl group" refers to a functional group containing carbon, hydrogen, and at least one heteroatom other than carbon and hydrogen. It includes heterocycloalkyl, heterocycloalkenyl (containing at least one carbon-carbon double bond), and heteroaryl. One or more ring-forming atoms in the ring are heteroatoms. The heteroatom can be O, N, S, or any combination thereof. They may be monocyclic, bicyclic or polycyclic. They may be Spiro rings or fused rings.

In the present invention, the term "substituent" includes, but is not limited to, fluorine, chlorine, bromine, cyano, hydroxyl, amino, $C_{1-6}$ hydrocarbyloxy group, $C_{1-6}$ halohydrocarbyl group, $C_{1-6}$ acyl group, and $C_{1-6}$ sulfonyl group.

The term "hydrocarbyloxy group" as used herein refers to an O-hydrocarbyl group, where the "hydrocarbyl group" is as defined above.

The term "hydrocarbyloxycarbonyl group" as used herein refers to a C(=O)O-hydrocarbyl group, in which the "hydrocarbyl group" is as defined above.

The term "amino group" as used herein refers to N(H or hydrocarbyl group 1) (H or hydrocarbyl group 2), in which the "hydrocarbyl group" is as defined above.

The term "aminocarbonyl group" as used herein refers to a C(=O)-amino group, in which the "amino group" is as defined above.

The term "amido group" as used herein refers to N(H or hydrocarbyl group)-C(=O)-hydrocarbyl group, in which the "hydrocarbyl group" is as defined above . . .

In the present invention, the term "containing", "comprising" or "including" means that various ingredients can be used together in the mixture or composition of the present invention. Thus, the terms "consisting essentially of and" consisting of are included in the term "containing".

In the present invention, the term "pharmaceutically acceptable" ingredient refers to a substance suitable for human and/or animals without excessive adverse side effects (such as toxicity, irritation and allergy), which means it has a reasonable benefit/risk ratio.

In the present invention, the term "effective amount" refers to an amount of a therapeutic agent to treat, alleviate or prevent a target disease or condition, or an amount that exhibits a detectable therapeutic or preventive effect. The exact effective amount for a certain subject will depend on the subject's size and health, the nature and extent of the condition, and the therapeutic agent and/or combination of therapeutic agents chosen for administration. Therefore, it is not useful to specify an accurate effective amount in advance. However, for a given condition, routine experimentation can be used to determine the effective amount, which can be determined by the clinician.

As used herein, unless specifically stated, the term "substituted" refers to the replacement of one or more hydrogen atoms on a group with substituent(s) selected from the group consisting of: halogen, unsubstituted or halogenated $C_{1-6}$ alkyl, unsubstituted or halogenated $C_{2-6}$ acyl, unsubstituted or halogenated $C_{1-6}$ alkyl-hydroxy.

Unless otherwise specified, all compounds present in the present invention are intended to include all possible optical isomers, such as a single chiral compound, or a mixture of various chiral compounds (i.e., a racemate). Among all the compounds of the present invention, each chiral carbon atom may optionally be in the R configuration or the S configuration, or a mixture of the R configuration and the S configuration.

As used herein, the term "compound of the present invention" refers to a compound of formula I. The term also includes various crystalline forms, pharmaceutically acceptable salts, hydrates or solvates of the compounds of formula I.

As used herein, the term "pharmaceutically acceptable salt" refers to a salt of a compound of the present invention with an acid or a base suitable for use as a drug. The pharmaceutically acceptable salts include inorganic and organic salts. One preferred kind of salt is a salt of a compound of the present invention with an acid. Suitable acids for forming salts include, but are not limited to, inorganic acids such as hydrochloric acid, hydrobromic acid, hydrofluoric acid, sulfuric acid, nitric acid, phosphoric acid, etc., organic acids such as formic acid, acetic acid, propionic acid, oxalic acid, malonic acid, succinic acid, fumaric acid, maleic acid, lactic acid, malic acid, tartaric acid, citric acid, picric acid, methanesulfonic acid, benzylsulfonic acid, benzenesulfonic acid, etc.; and acidic amino acids such as aspartic acid, glutamic acid, etc.

Compounds and Pharmaceutically Acceptable Salts Thereof

The present invention relates to a compound of formula I shown as below or a pharmaceutically acceptable salt thereof;

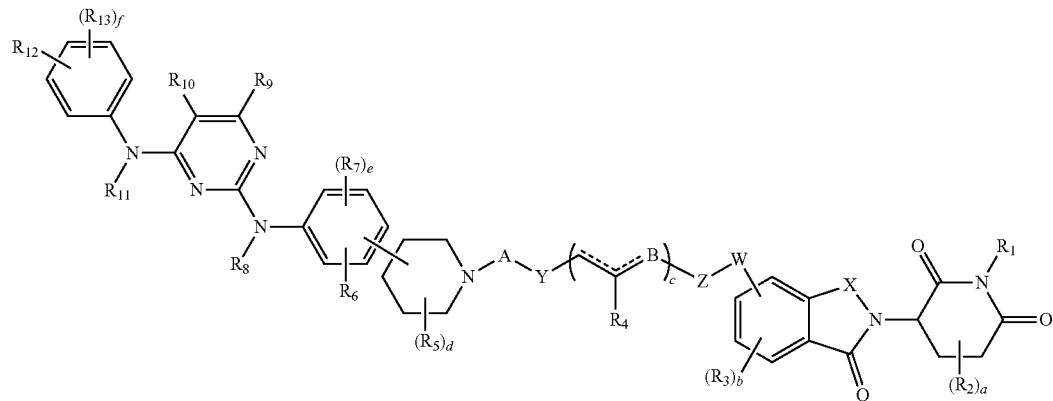

I wherein,

— refers to a single bond;

═ refers to a single or double bond; A is missing or selected from C(=O), C(=O)X1-, SOX1-, SO$_2$X1-, $C_{1-8}$ hydrocarbyl group with or without substituent(s), $C_{1-8}$ cyclic hydrocarbyl group with or without substituent(s), and $C_{1-8}$ heterocyclic hydrocarbyl group with or without substituent(s); wherein X1 is missing or selected from $(CR_{35}R_{36})_kO$, $(CR_{35}R_{36})_kS$ and $NR_{14}$; wherein $R_{35}$, $R_{36}$, $R_{14}$ is each independently selected from H, $C_{1-8}$ hydrocarbyl group with or without substituent(s), $C_{1-8}$ cyclic hydrocarbyl group with or without substituent(s), and $C_{1-8}$ heterocyclic hydrocarbyl group with or without substituent(s); k is an integer between 0 and 3;

W is missing or selected from O, $NR_{17}$, —X2C(=O)X3, and —X2S(=O)$_g$X3; wherein $R_{17}$ is H, $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s); wherein X2, X3 is each independently missing or selected from O, S, and $NR_{18}$; wherein g is an integer between 0 and 2; wherein $R_{18}$ is H, $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s);

Y is $(CR_{22}R_{23})_h$, $CHX4(CR_{22}R_{23})_h$, $CX4\text{-}CH(CR_{22}R_{23})_h$, or $(CR_{22}R_{23})_h$; wherein h is an integer between 0 and 30; wherein $R_{22}$, $R_{23}$ is each independently selected from H, cyano, hydroxyl, amino, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s), and $C_{1-8}$ hydrocarbyloxy group with or without substituent(s); wherein X4 is H, halogen, cyano, nitro, hydroxyl, $C_i$s hydrocarbyloxy group with or without substituent(s), $C_{1-8}$ hydrocarbyloxycarbonyl group with or without substituent(s), $C_{1-8}$ amino group with or without substituent(s), $C_{1-8}$ ester group with or without substituent(s), $C_{1-8}$ aminocarbonyl group with or without substituent(s), $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s);

Z is $(CR_{24}R_{25})_i$, $CHX5(CR_{24}R_{25})_i$, $CX5\text{-}CH(CR_{24}R_{25})$, or $C=C(CR_{24}R_{25})$; wherein i is an integer between 0 and 30; wherein $R_{24}$, $R_{25}$ is each independently selected from H, cyano, hydroxyl, amino, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s), and $C_{1-8}$ hydrocarbyloxy group with or without substituent(s); wherein X5 is H, halogen, cyano, nitro, hydroxyl, $C_{1-8}$ hydrocarbyloxy group with or without substituent(s), $C_{1-8}$ hydrocarbyloxycarbonyl group with or without substituent(s), $C_{1-8}$ amino group with or without substituent(s), $C_{1-8}$ ester group with or without substituent(s), $C_{1-8}$ aminocarbonyl group with or without substituent(s), $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s);

B is missing or selected from O, C=O, S, $NR_{15}$, —$NR_{15}C(=O)$—, —$C(=O)NR_{15}$—, —$C(=O)O$—, $OC(=O)O$, —$NR_{15}C(=O)O$—, —$OC(=O)NR_{15}$—, —$NR_{15}C(=O)NR_{16}$—, $C_{1-12}$ hydrocarbyl group with or without substituent(s), $C_{1-12}$ cyclic hydrocarbyl group with or without substituent(s), and $C_{1-12}$ heterocyclic hydrocarbyl group with or without substituent(s); wherein $R_{15}$, $R_{16}$ is each independently selected from H, $C_{1-8}$ hydrocarbyl group with or without substituent(s), $C_{1-8}$ cyclic hydrocarbyl group with or without substituent(s), and $C_{1-8}$ heterocyclic hydrocarbyl group with or without substituent(s);

X is selected from $CR_{19}R_{20}$, C(=O), S(=O), $SO_2$, and $NR_{21}$; wherein $R_{19}$, $R_{20}$ is each independently selected from II, cyano, hydroxyl, amino, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s), and $C_{1-8}$ hydrocarbyloxy group with or without substituent(s); wherein $R_{21}$ is selected from H, $C_{1-8}$ hydrocarbyl group with or without substituent(s), $C_{1-8}$ cyclic hydrocarbyl group with or without substituent(s), and $C_{1-8}$ heterocyclic hydrocarbyl group with or without substituent(s);

$R_1$, $R_8$, $R_{11}$ is each independently selected from II, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s) and $C_{1-6}$ acyl group with or without substituent(s);

$R_2$, $R_5$ is each independently selected from hydrogen, $OR_{26}$, $NR_{27}R_{28}$, cyano, halogen, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s), $C_{1-6}$ acyl group with or without substituent(s) and $C_{1-6}$ amido group with or without substituent(s); wherein $R_{26}$, $R_{27}$, $R_{28}$ is each independently selected from H, $C_{1-8}$ hydrocarbyl group with or without substituent(s), $C_{1-8}$ cyclic hydrocarbyl group with or without substituent(s), and $C_{1-8}$ heterocyclic hydrocarbyl group with or without substituent(s);

$R_3$, $R_6$, $R_7$, $R_9$, $R_{10}$, $R_{12}$, $R_{13}$ is each independently selected from H, $OR_{29}$, $NR_{30}R_{31}$, cyano, halogen, nitro, $C_{1-8}$ hydrocarbyl group with or without substituent(s), cyclic hydrocarbyl group with or without substituent(s), heterocyclic hydrocarbyl group with or without substituent(s), $X6S(=O)_jR_{32}$, and $X6C(=O)R_{33}$; wherein j is an integer between 0 to 2; wherein $R_{29}$, $R_{30}$, $R_{31}$, $R_{32}$, $R_{33}$ is each independently selected from II, $C_{1-8}$ hydrocarbyl group with or without substituent(s), $C_{1-8}$ cyclic hydrocarbyl group with or without substituent(s) and $C_{1-8}$ heterocyclic hydrocarbyl group with or without substituent(s); wherein X6 is missing or selected from O, S, and $NR_{34}$; wherein $R_{34}$ is H, $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s);

$R_4$ is selected from H, cyano, carboxyl, $C_{1-8}$ hydrocarbyl group with or without substituent(s), and $C_{1-8}$ hydrocarbyloxycarbonyl group with or without substituent(s);

a is an integer between 0 and 5;
b is an integer between 0 and 3;
c is an integer between 0 and 30;
d is an integer between 0 and 9;
e is an integer between 0 and 3;
f is an integer between 0 and 4.

In a preferred embodiment of the invention, the compound is selected from the group consisting of:

| Compound No. | Structure of compound |
|---|---|
| 3 | 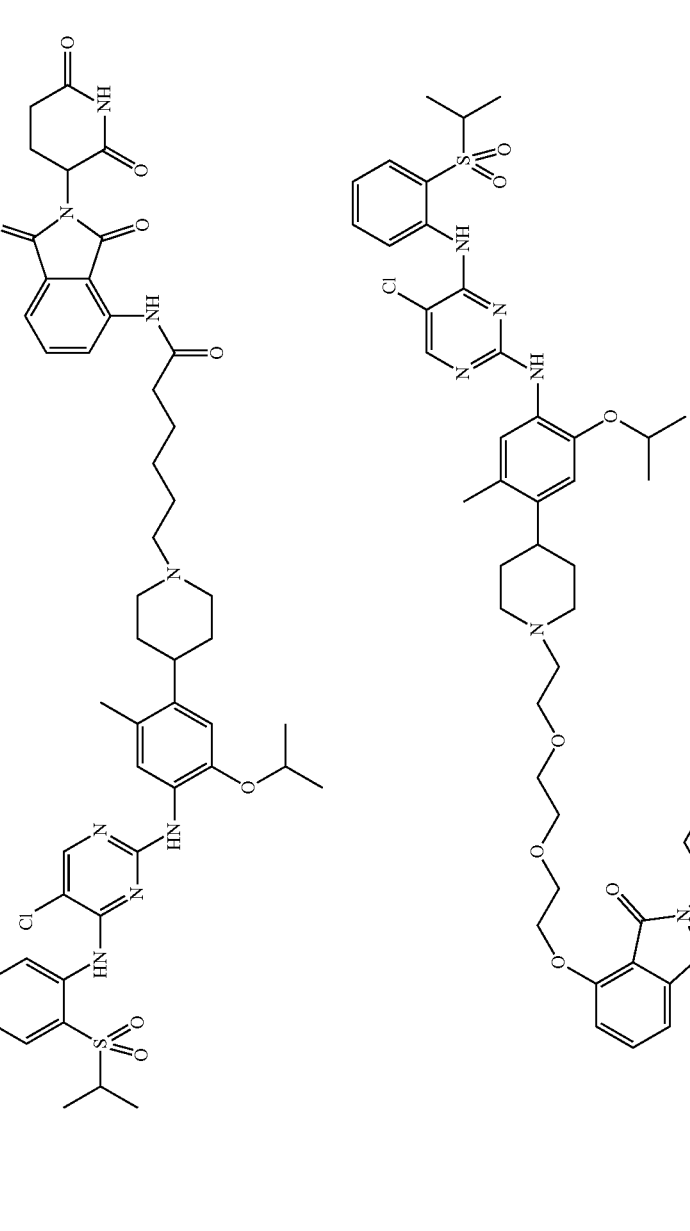 |
| 7 | 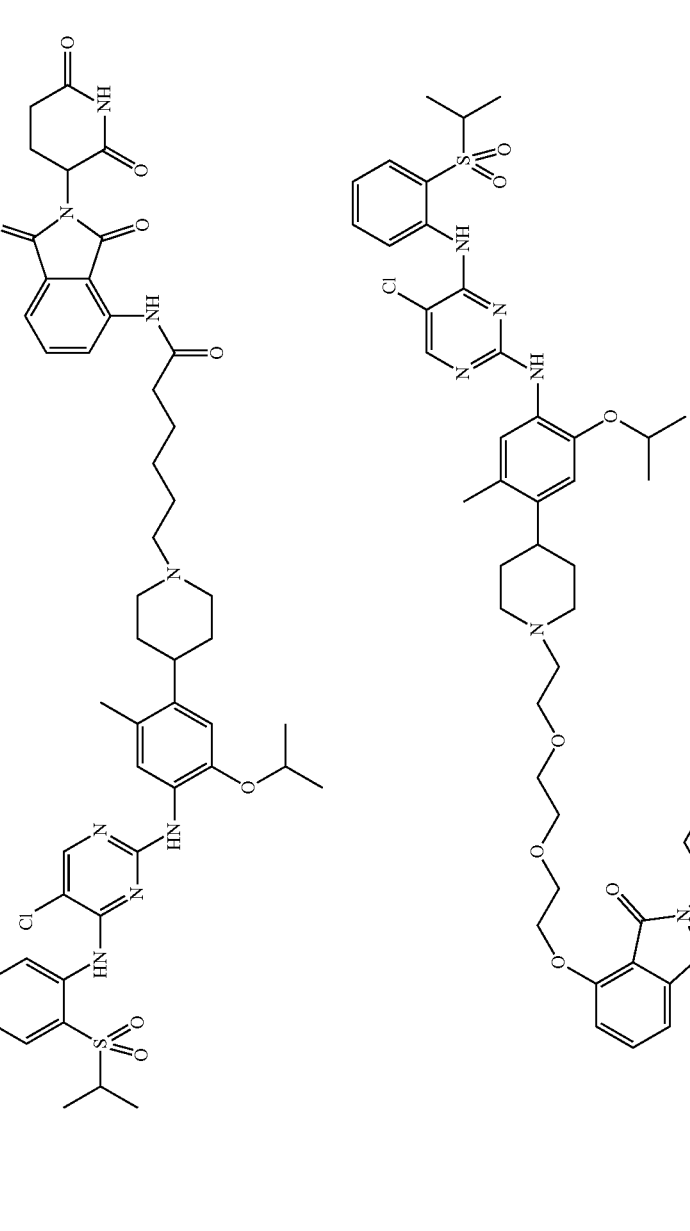 |

-continued
| Compound No. | Structure of compound |
|---|---|
| 10 | 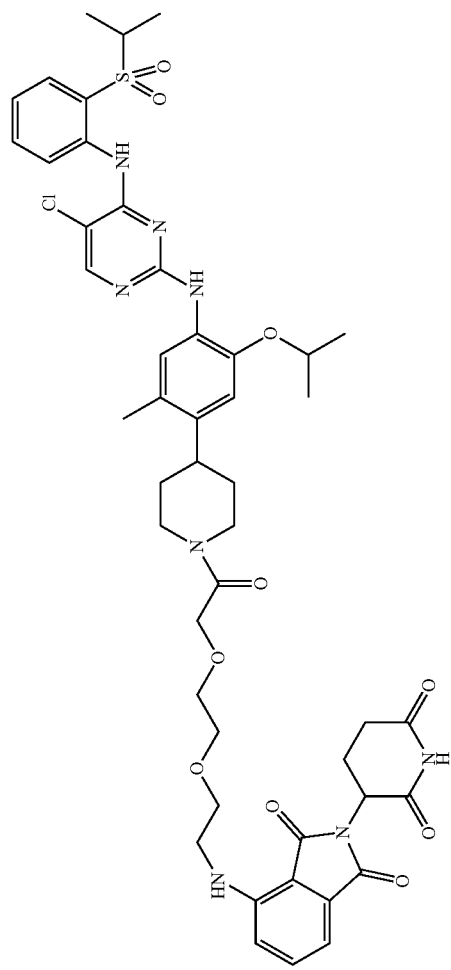 |
| 13 | 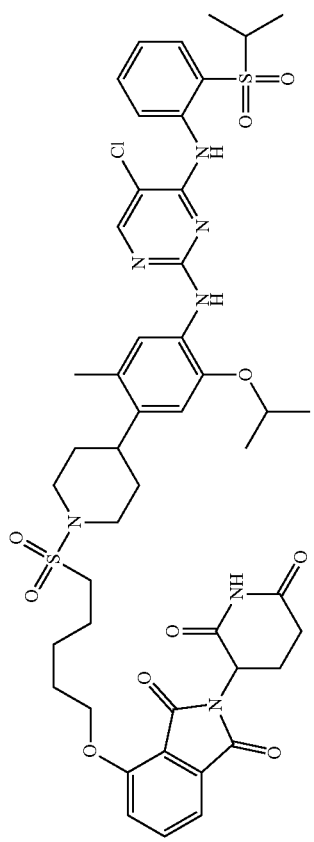 |

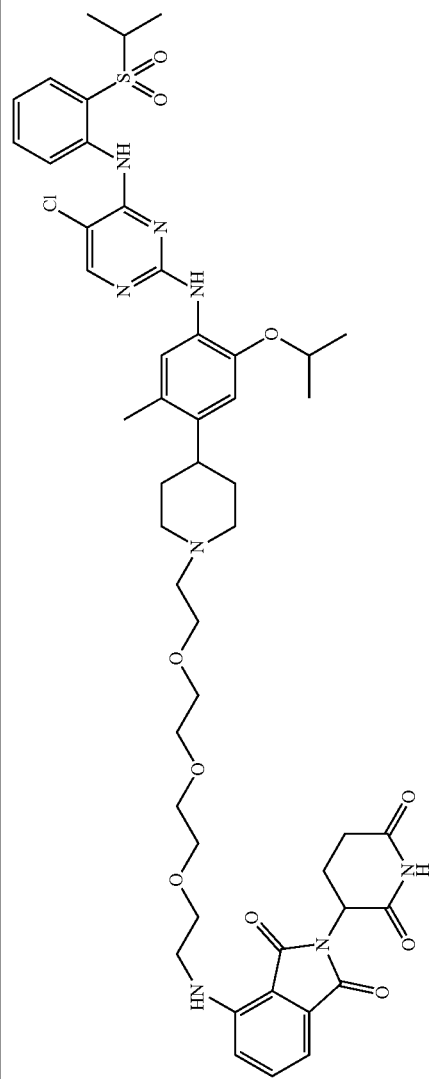

-continued
| Compound No. | Structure of compound |
|---|---|
| 16 | 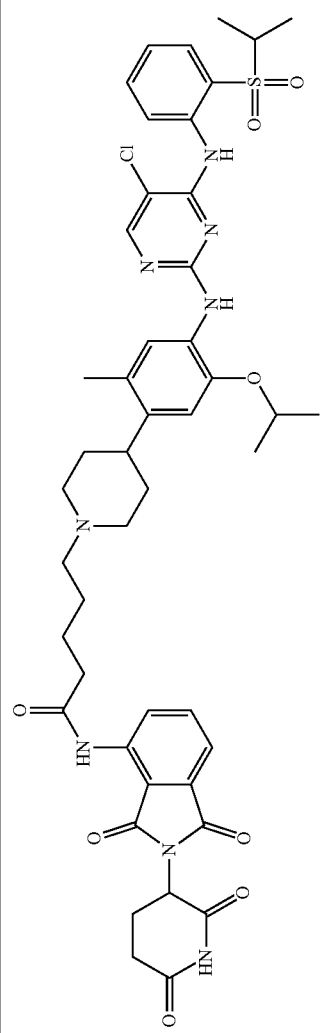 |
| 17 | 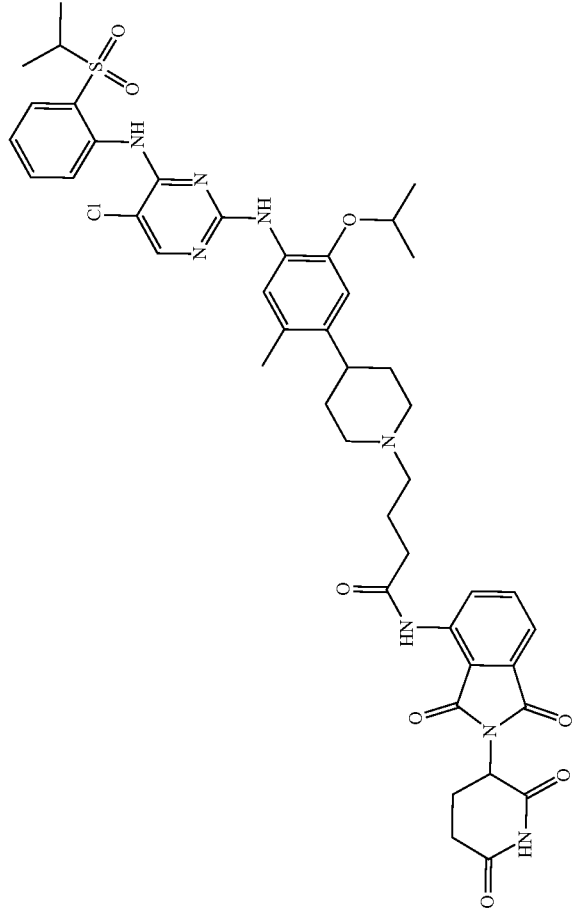 |

-continued
| Compound No. | Structure of compound |
|---|---|
| 18 | 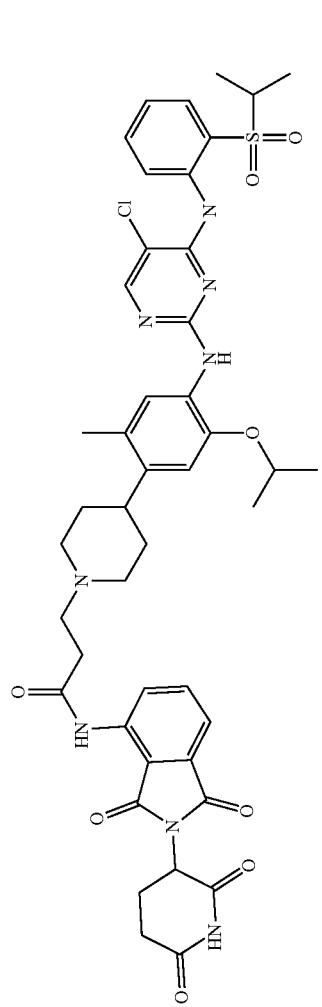 |
| 19 | 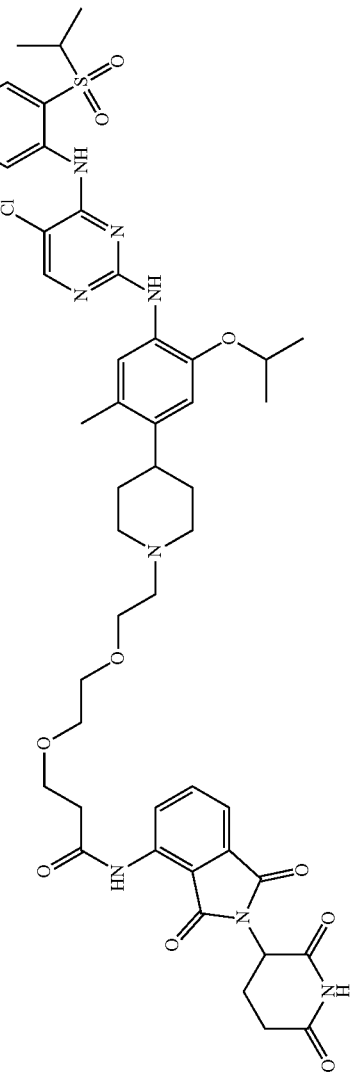 |

-continued
| Compound No. | Structure of compound |
|---|---|
| 20 | 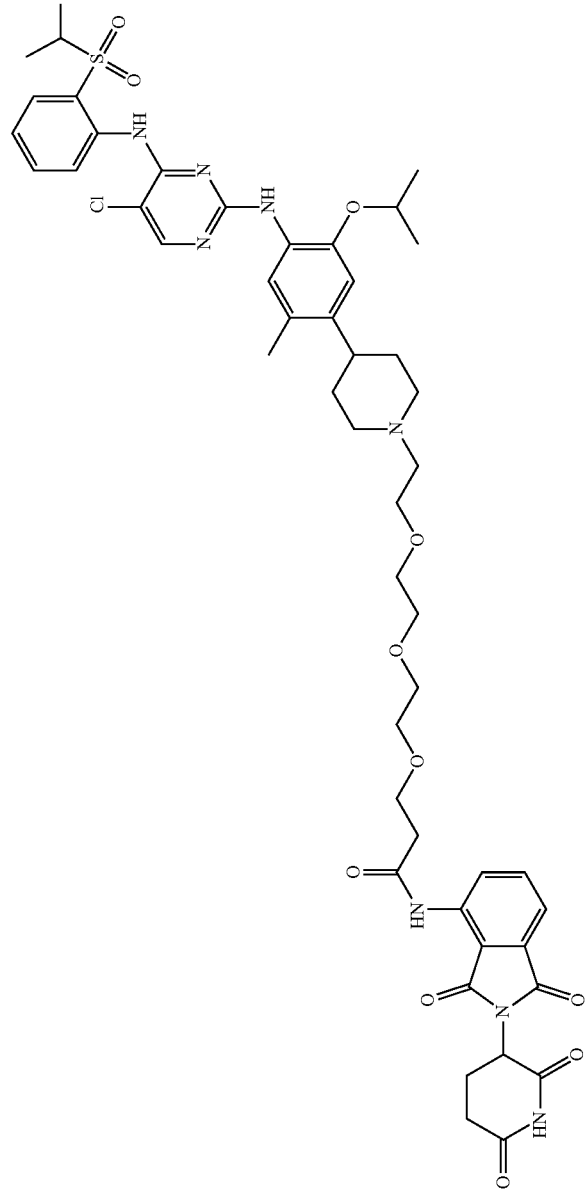 |
| 21 | 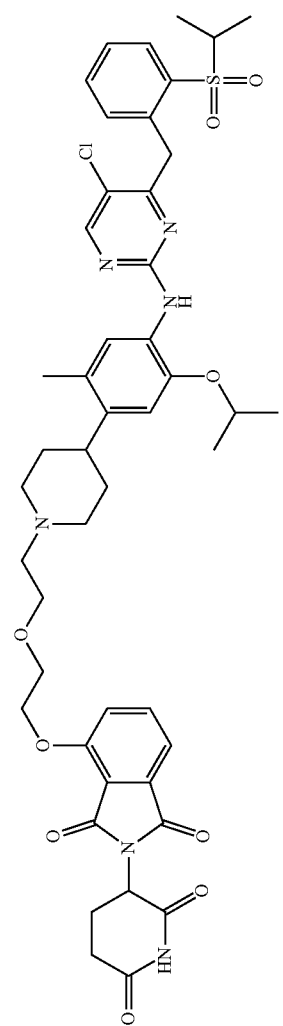 |

-continued
| Compound No. | Structure of compound |
|---|---|
| 22 | 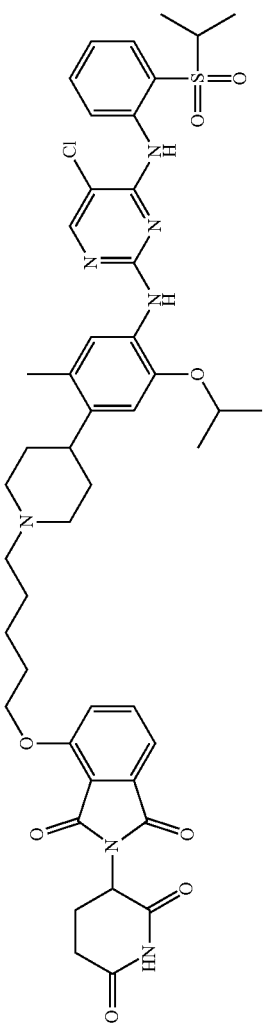 |
| 23 | 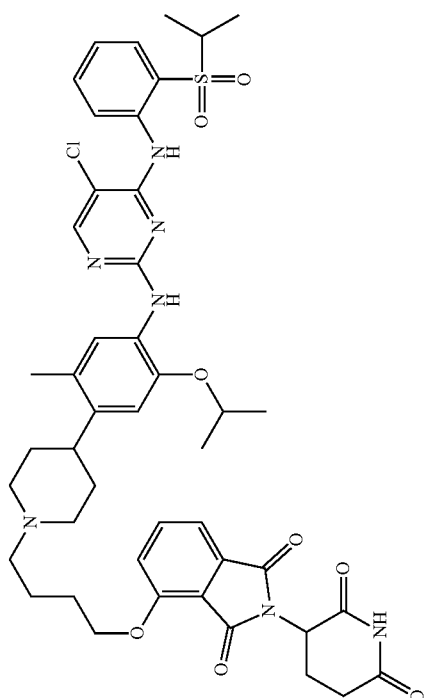 |
| 24 | 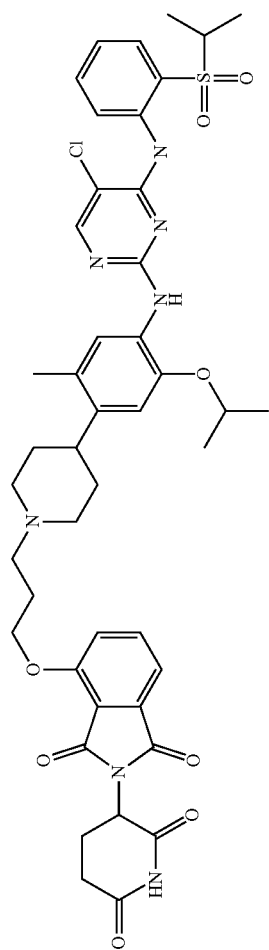 |

-continued
| Compound No. | Structure of compound |
|---|---|
| 25 | 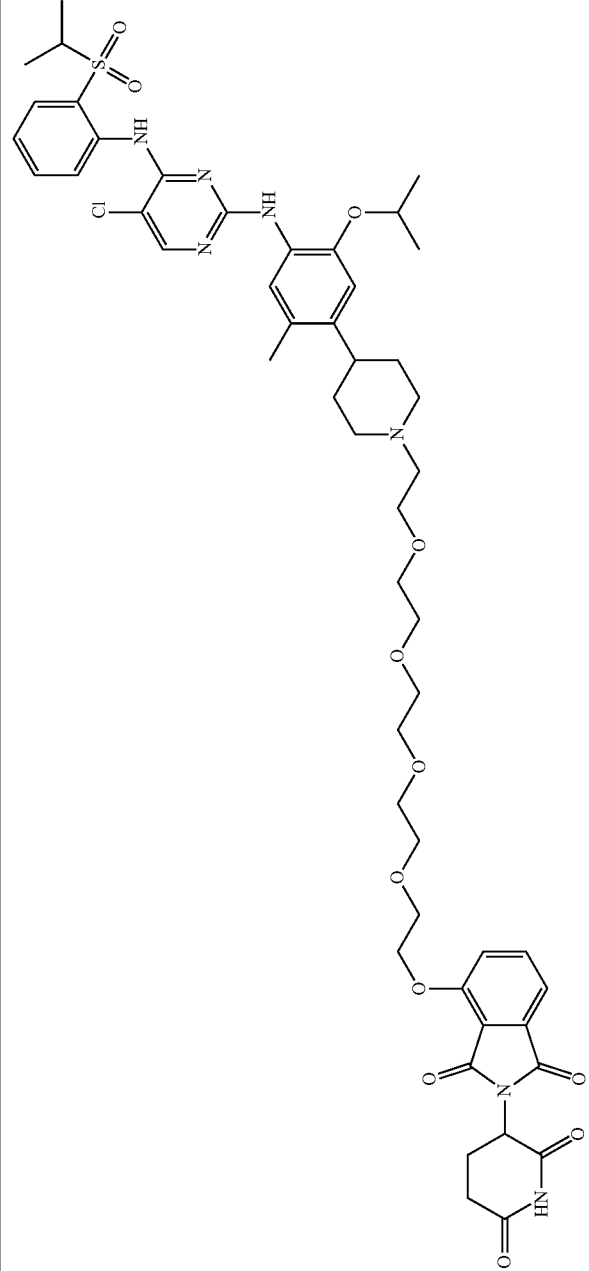 |

-continued
| Compound No. | Structure of compound |
|---|---|
| 26 | 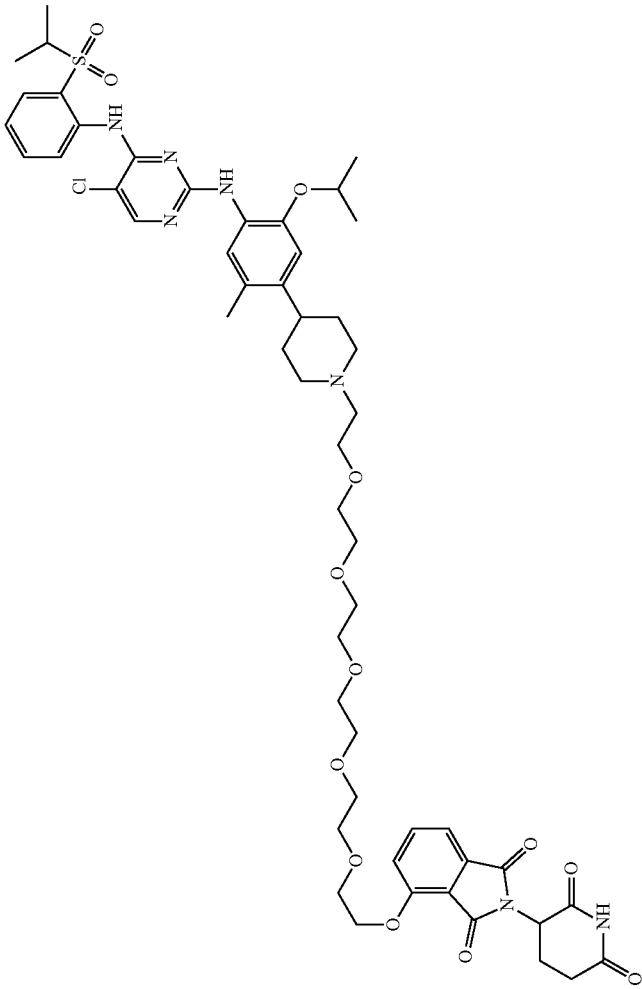 |
| 27 | 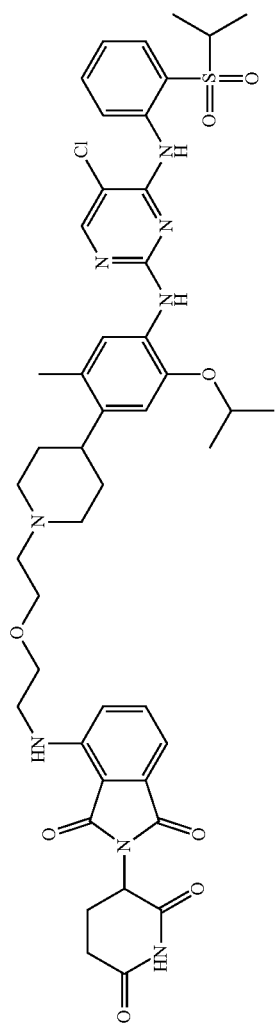 |

-continued
| Compound No. | Structure of compound |
|---|---|
| 28 | 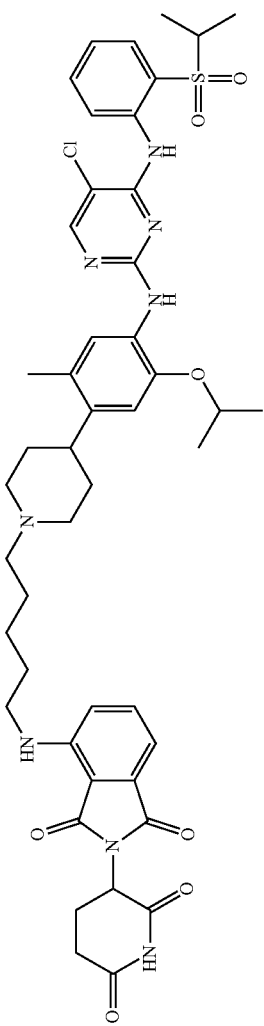 |
| 29 | 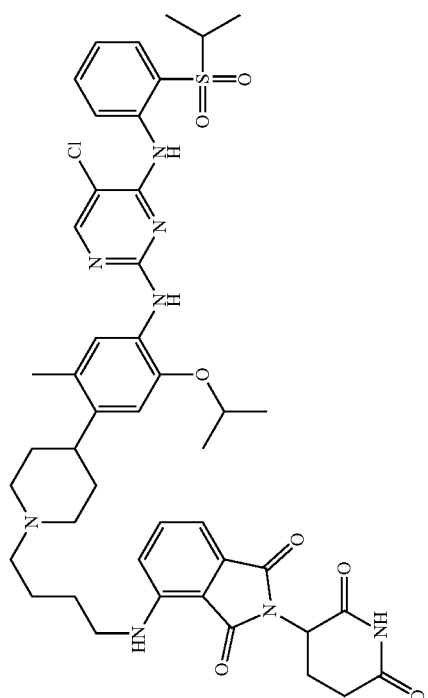 |
| 30 | 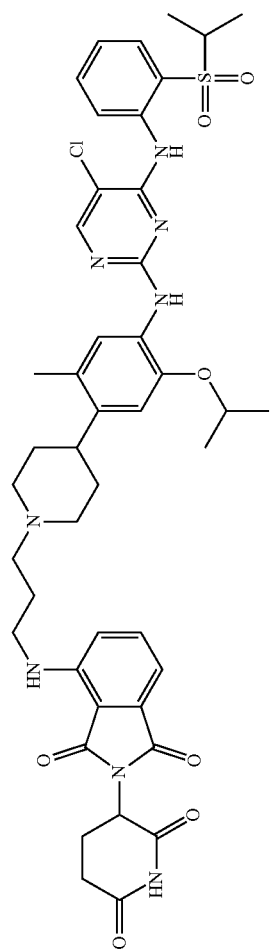 |

-continued
| Compound No. | Structure of compound |
|---|---|
| 31 | 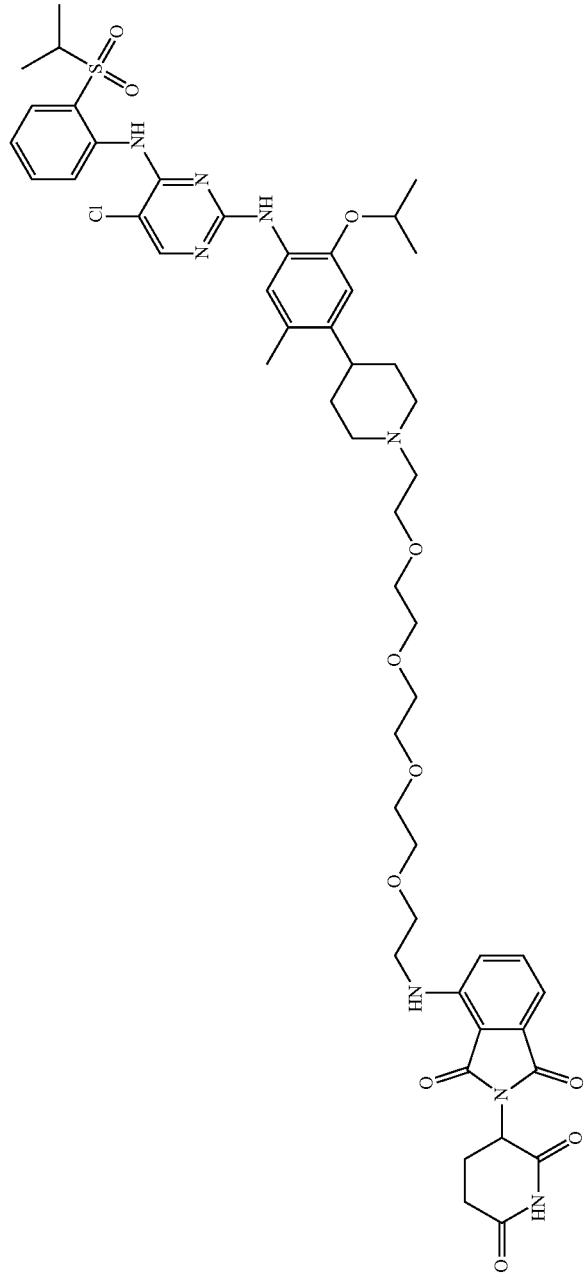 |

-continued
| Compound No. | Structure of compound |
|---|---|
| 32 | 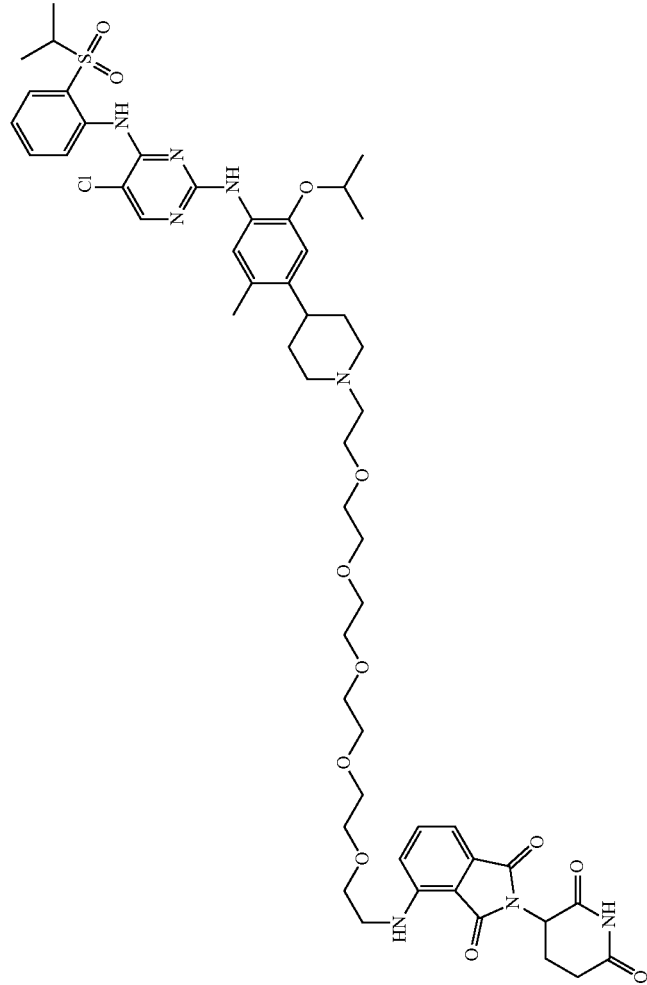 |
| 33 | 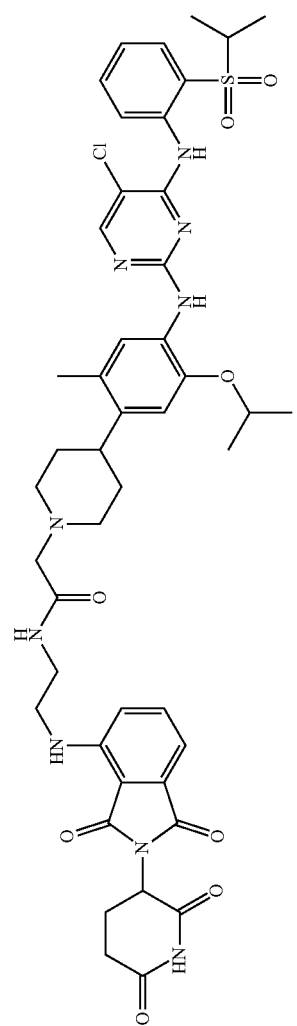 |

-continued
| Compound No. | Structure of compound |
|---|---|
| 34 | 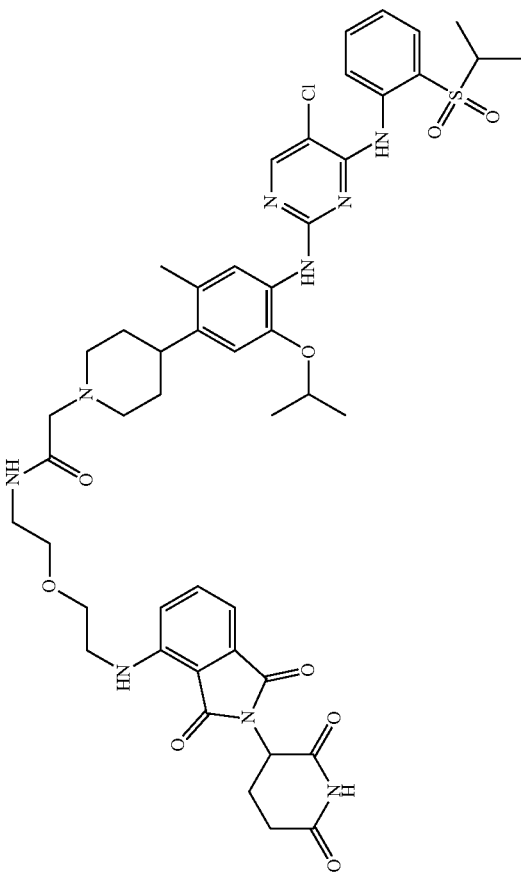 |
| 35 | 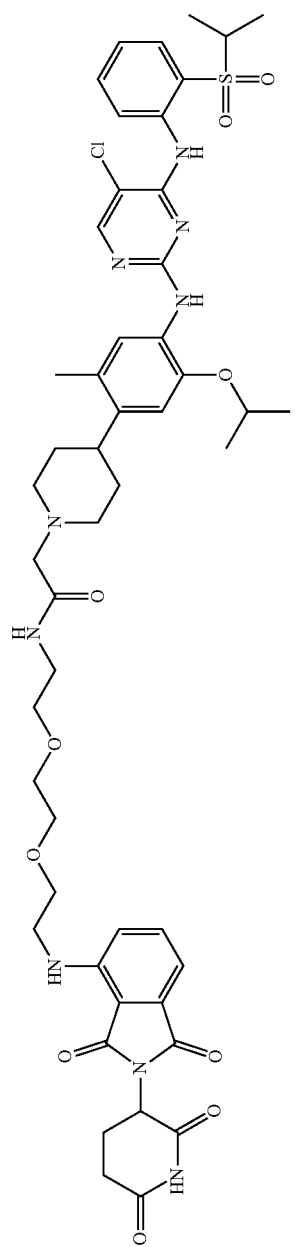 |

-continued
| Compound No. | Structure of compound |
|---|---|
| 36 | 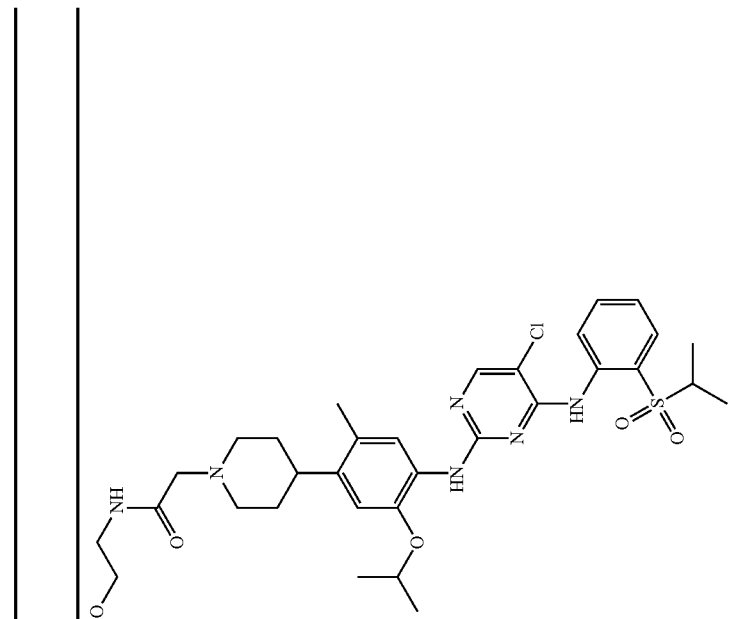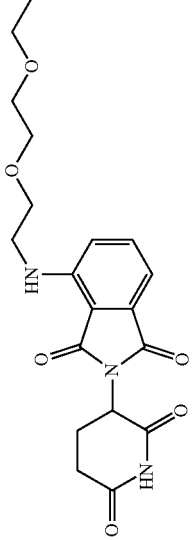 |
| 37 | 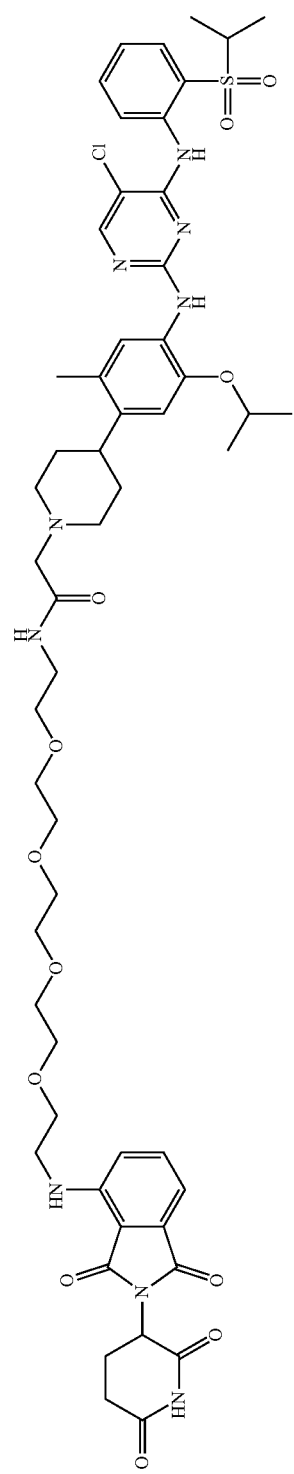 |

-continued
| Compound No. | Structure of compound |
|---|---|
| 38 | 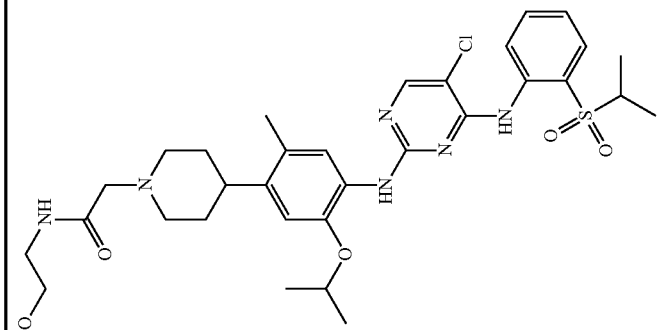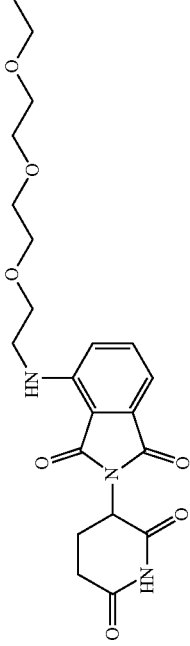 |
| 39 | 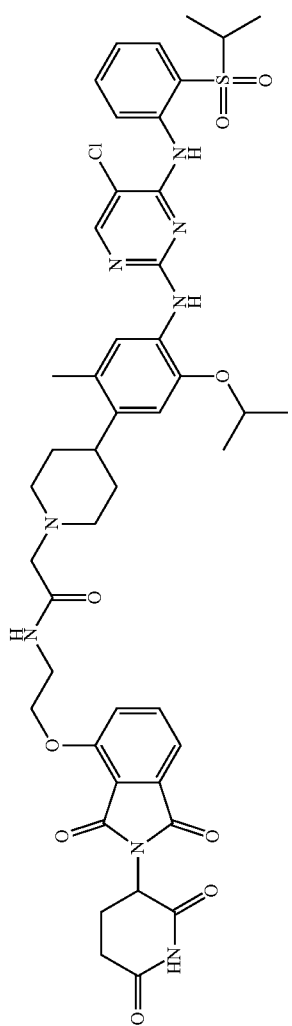 |

-continued
| Compound No. | Structure of compound |
|---|---|
| 40 | 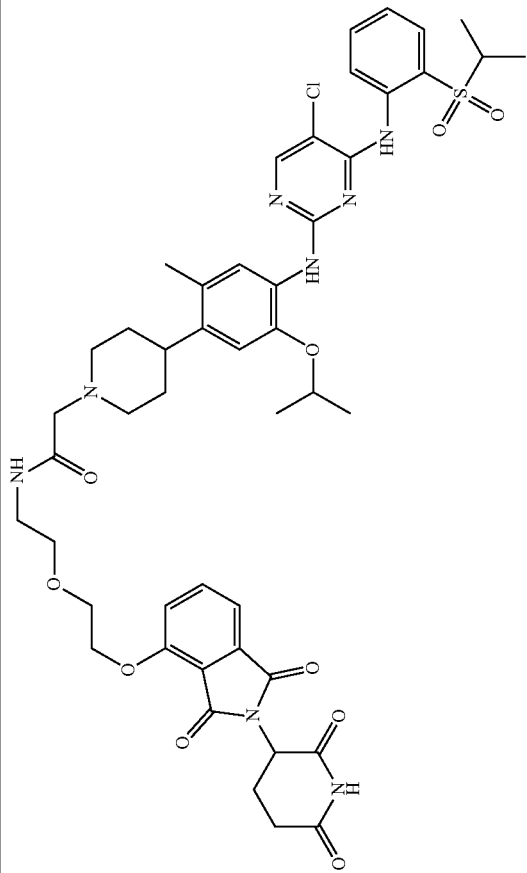 |
| 41 | 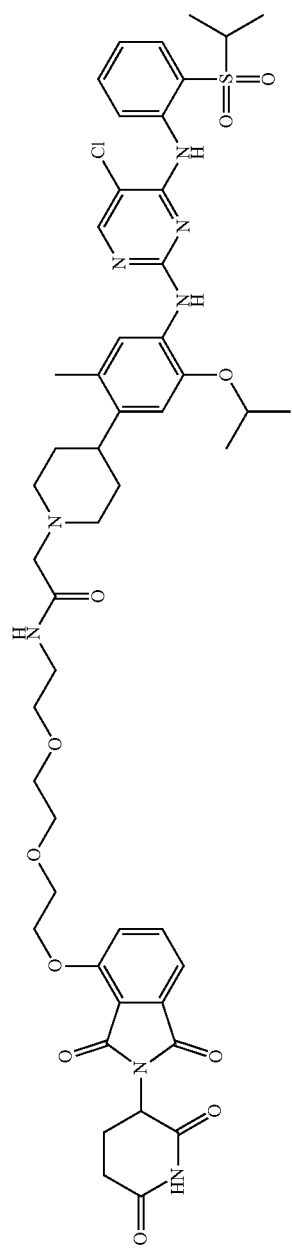 |

| Compound No. | Structure of compound |
|---|---|
| 42 | 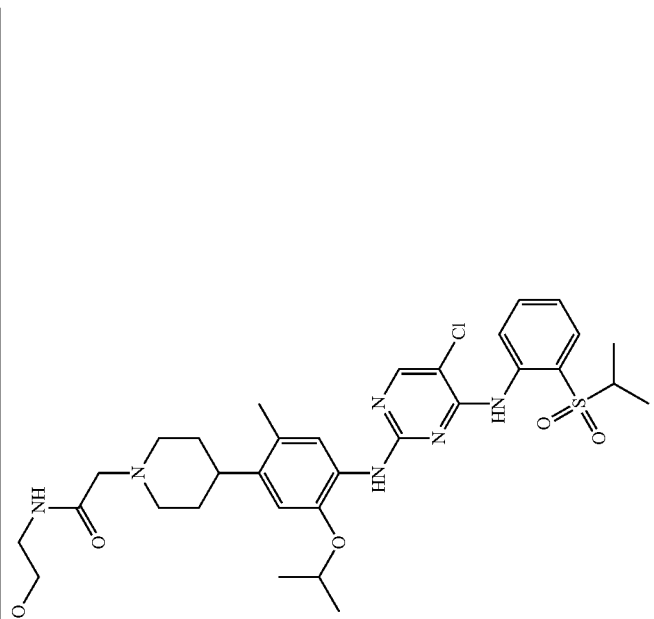 |
| 43 | 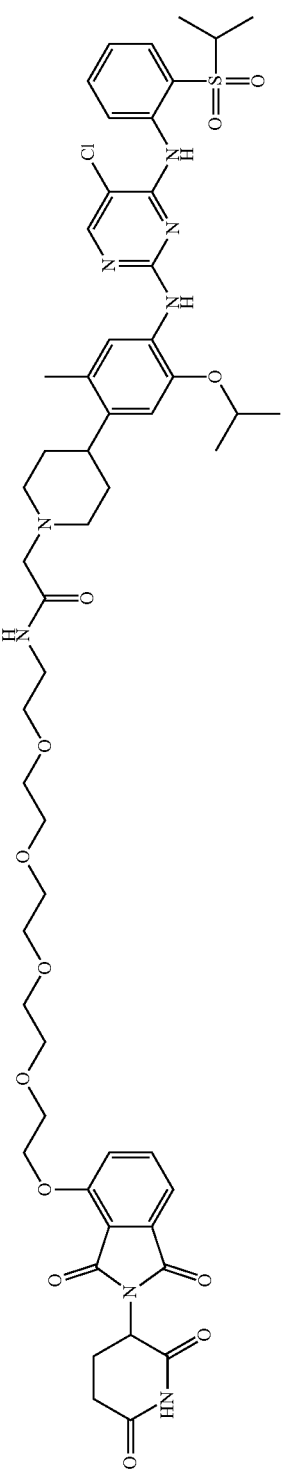 |

-continued
| Compound No. | Structure of compound |
|---|---|
| 44 | 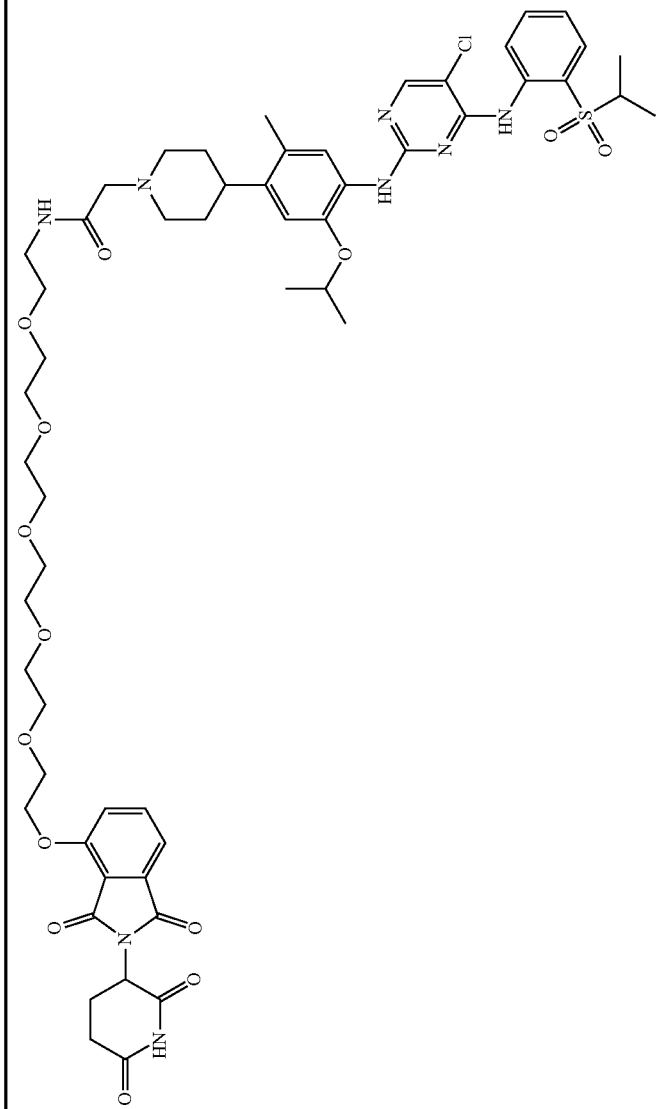 |

-continued
| Compound No. | Structure of compound |
|---|---|
| 45 | 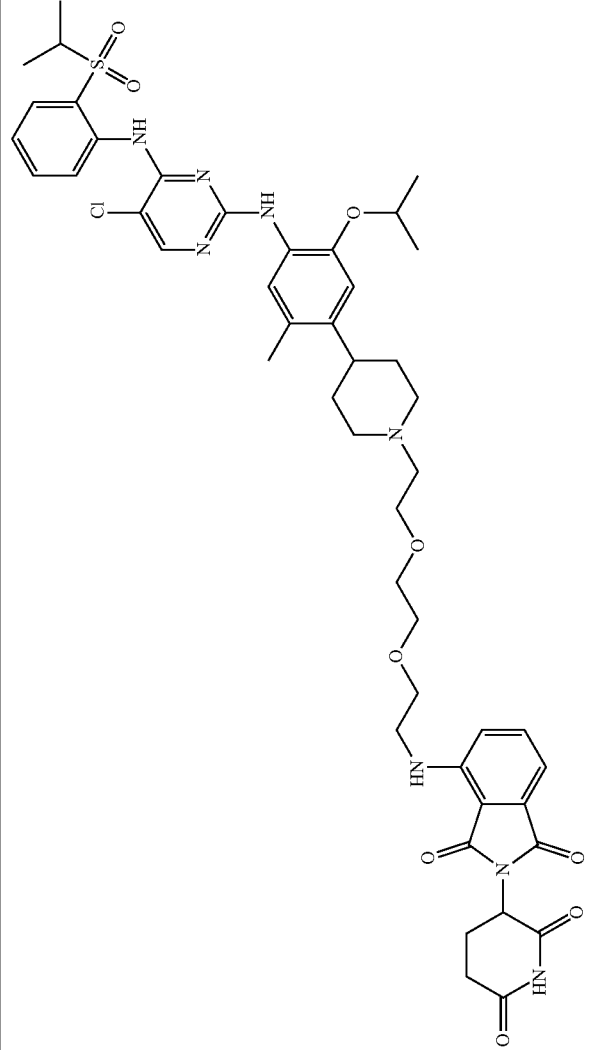 |

The compound of the present invention may form a pharmaceutically acceptable salt with an inorganic acid, an organic acid or a base. The inorganic acid includes, but is not limited to, hydrochloric acid, hydrobromic acid, nitric acid, perchloric acid, sulfuric acid, phosphoric acid and the like; the organic acid includes, but is not limited to, methanesulfonic acid, trifluoromethanesulfonic acid, ethanesulfonic acid, benzenesulfonic acid, p-toluenesulfonic acid, fumaric acid, oxalic acid, acetic acid, maleic acid, ascorbic acid, lactic acid, tartaric acid, malonic acid, glycolic acid, succinic acid, propionic acid and the like; the base includes, but is not limited to, an inorganic salt and an amine.

The term of a pharmaceutically acceptable salt refers to those salts which, according to medical judgment, are suitable for use in contact with human and mammalian tissues without excessive toxicity, irritation, allergic reactions, and the like. Pharmaceutically acceptable salts are well known in the art.

The present invention also encompasses pharmaceutical compositions containing a prodrug of a compound of formula I. Prodrugs include such compounds in which the precursor molecule is covalently bonded to the free carboxyl, hydroxyl, or amino group of the compound of formula I via a carbonate bond, a urethane bond, an amido bond, an alkyl ester bond, a phosphate bond, or a phosphoramidate bond.

Preparation of Compound
Preparation Method

The method for preparing the compound of formula I according to the present invention is described in more detail below, but these specific methods do not constitute any limitation to the present invention. The compound of the present invention can also be conveniently prepared by combining various synthetic methods described in the specification or known in the art, and such combination can be easily performed by those skilled in the art to which the present invention belongs.

The following reaction schemes illustrate the preparation of compounds of the present invention. Unless otherwise indicated, A, B, W, X, Y, Z, a, b, c, d, e, f, $R_1$, $R_2$, $R_3$, $R_4$, $R_5$, $R_6$, $R_7$, $R_8$, $R_9$, $R_{10}$, $R_{11}$, $R_{12}$, $R_{13}$ in the reaction scheme and subsequent discussions are as defined above. W1 is hydroxyl, amino, or $C_{1-8}$ hydrocarbyl group containing a reactive substituent (such as hydroxyl, amino, etc.); A' is a corresponding halide, carboxylic acid, acyl halide, acid anhydride, ester, amide, isocyanate, sulfonyl chloride, sulfonate, sulfinyl chloride, aminosulfuryl chloride, aldehyde, ketone, α, β unsaturated carbonyl compound, etc. that can form A; Z' is a corresponding alcohol, halide, carboxylic acid, acyl halide, acid anhydride, ester, amide, isocyanate, sulfonyl chloride, sulfonate, sulfinyl chloride, aminosulfuryl chloride, aldehyde, ketone, α, β unsaturated carbonyl compound, etc. that can form —Z—W— with W1.

In a preferred embodiment of the present invention, the method for preparing a compound of formula I provided by the present invention includes the steps:

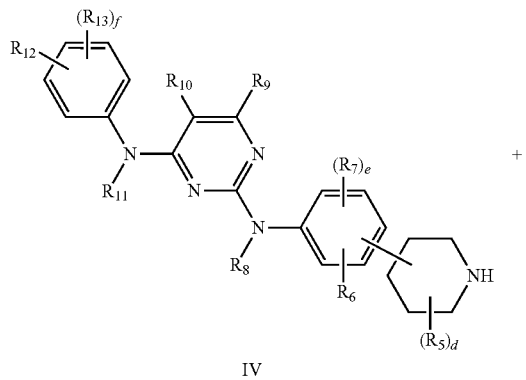

IV

+

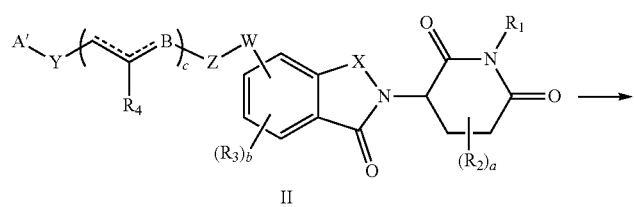

II

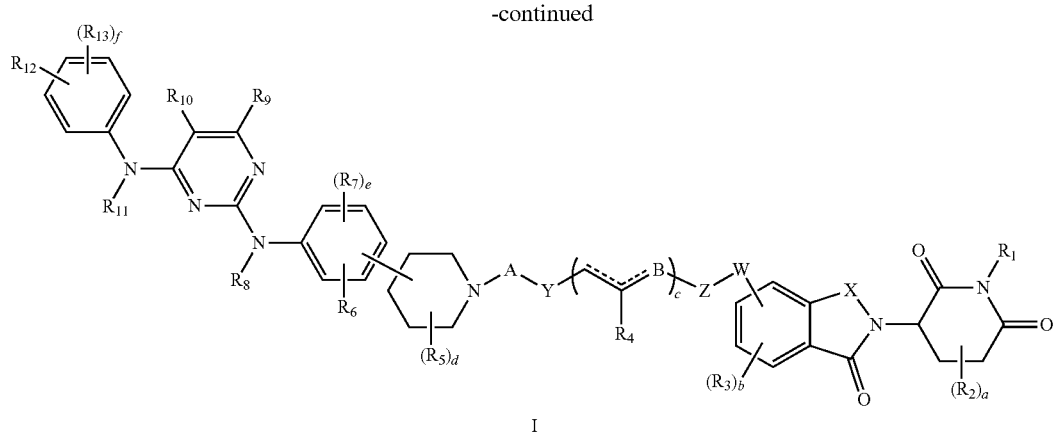

I (a) reacting a compound of formula IV and a compound of formula II in an inert solvent to obtain a compound of formula I;

wherein, each group is defined as described above.

In another preferred example, the method further includes the step of:

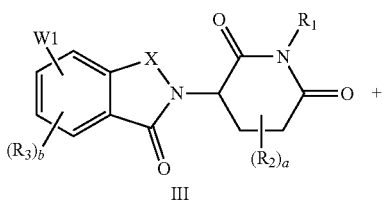

III

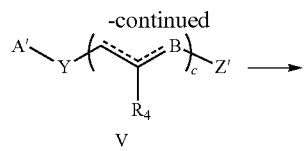

V

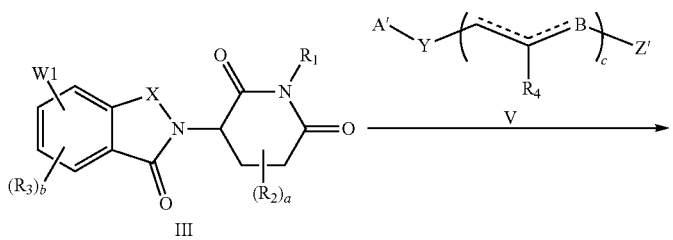

II (b) reacting a compound of formula III and a compound of formula V in an inert solvent to obtain a compound of formula I.

In general, compounds of formula I can be obtained from those of formula III as described in the following schemes:

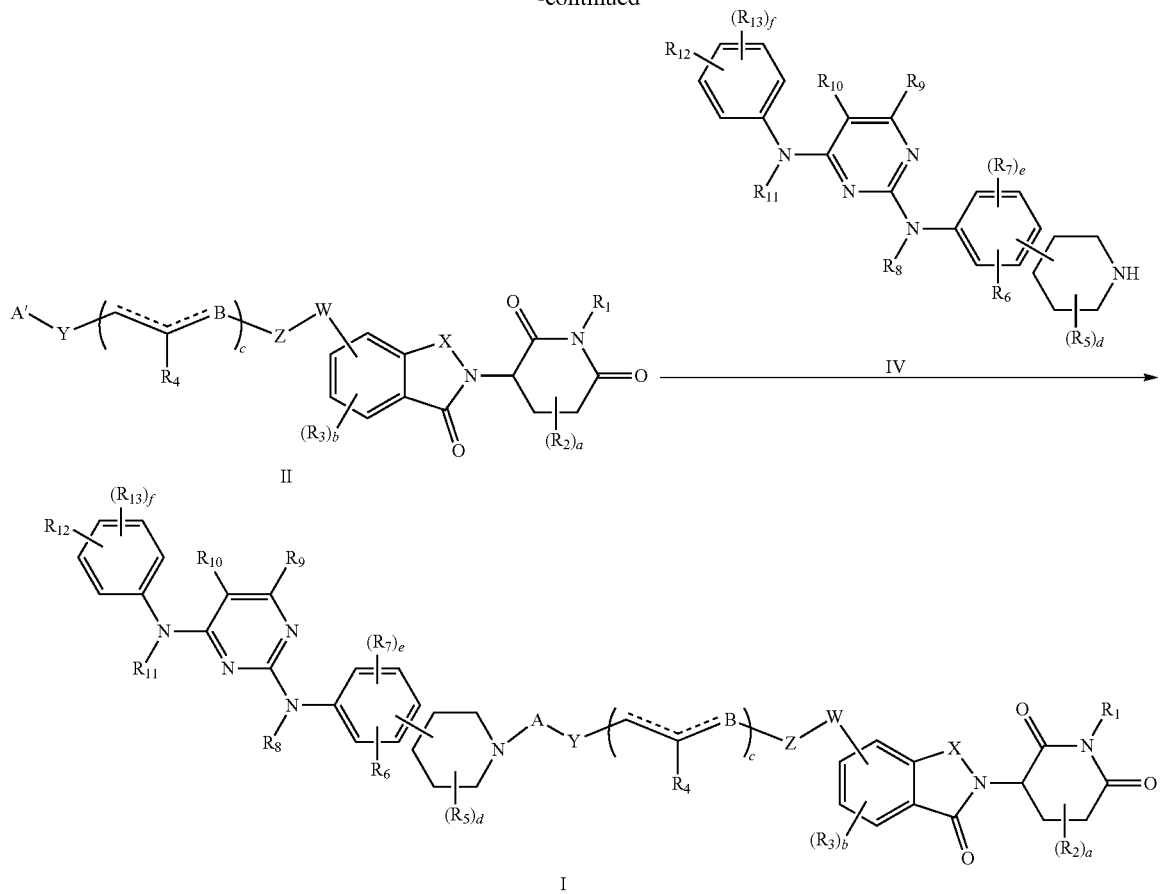

In compound II, when W is an ether, it can be prepared by directly nucleophilic substitution of formula III (W1=OH) with an intermediate containing a leaving group under the action of a base, or by a photo-extension reaction with an alcohol; when W is an ester or carbamate (NHCO$_2$), it can be prepared by reacting formula III (W1=OH) with an acyl chloride, an activated ester (amide), a carboxylic acid, or an isocyanate under the action of a base; when W is an amine, it can be prepared by directly nucleophilic substitution of formula III (W1=NH$_2$) with an intermediate containing a leaving group under the action of a base, or by reductive amination reaction of formula III (W1=NH$_2$) with an aldehyde/ketone; when W it is an amide, alkoxycarbonylamine (OCONH) or urea, it can be prepared by reacting formula III (W1=NH$_2$) with the corresponding acyl chloride, activated ester (amide), carboxylic acid and isocyanate under the action of a base.

In compound I, when A and a nitrogen atom are connected through a C—N bond, it can be prepared by direct substitution reaction or reductive amination reaction; when A and a nitrogen atom are connected in the form of amide, urea, carbamate, sulfonamide, or sulfamide, it can be prepared by using the corresponding acyl chloride, activated ester (amide), carboxylic acid, isocyanate, sulfonyl chloride, or sulfuryl chloride.

Generally, according to the connection structure of A and W, compound I can also be obtained by first connecting formula IV to the middle chain and then reacting with formula III. The chemical synthesis method used is the same as described above.

Compounds of formula III or IV can be obtained by known synthetic methods or can be easily obtained commercially.

Use of Compounds of Formula I

The compounds of formula I can be used for one or more of the following purposes:

(a) preparation of drugs for the treatment of diseases related to the activity or expression level of anaplastic lymphoma kinase (ALK);

(b) preparation of anaplastic lymphoma kinase (ALK) targeted inhibitors or degradation agents;

(c) non-therapeutic inhibition or degradation of anaplastic lymphoma kinase (ALK) in vitro;

(d) non-therapeutic inhibition of tumor cell proliferation in vitro; and/or (e) treatment of diseases related to the activity or expression level of anaplastic lymphoma kinase (ALK).

In another preferred example, the disease related to the activity or expression level of anaplastic lymphoma kinase (ALK) is a tumor, preferably the tumor is selected from the group consisting of non-small cell lung cancer, inflammatory myofibroblastoma etc. . . . .

The compound of formula I of the present invention can be used to prepare a pharmaceutical composition, which comprises: (i) an effective amount of a compound of formula I, or a pharmaceutically acceptable salt thereof; and (ii) a pharmaceutically acceptable carrier.

In another preferred example, the effective amount refers to a therapeutically effective amount or an inhibitory effective amount.

The compound of formula I of the present invention can also be used in a method for inhibiting or degrading anaplastic lymphoma kinase (ALK), and the inhibition is a non-therapeutic inhibition in vitro or a therapeutic inhibition.

In another preferred example, when an inhibitory effective amount of the compound of formula I of the present invention or a pharmaceutically acceptable salt thereof is administered to an inhibitory subject, the inhibitory effective amount is 0.001-500 nmol/L, preferably 0.01-200 nmol/L.

In particular, the present invention also provides a method of treating a disease related to the activity or expression level of anaplastic lymphoma kinase (ALK), and the method comprises: administering a therapeutically effective amount of a compound of formula I or a pharmaceutical composition containing the compound of formula I as an active ingredient to a subject in need of treatment.

Pharmaceutical Composition and Administration

Since the compound of the present invention has excellent inhibitory activity on anaplastic lymphoma kinase (ALK), the compound of the present invention and its various crystal forms, pharmaceutically acceptable inorganic or organic salts, hydrates or solvates and the pharmaceutical composition containing the compound of the present invention as a main active ingredient can be used for treating, preventing, and alleviating diseases related to Alk activity or expression level. According to the prior art, the compounds of the present invention are useful for treating diseases including tumors and the like.

The pharmaceutical composition of the present invention comprises the compound of the present invention or the pharmaceutically acceptable salt thereof in a safe and effective amount range and pharmaceutically acceptable excipients or carriers. The "safe and effective amount" means: the amount of the compound is sufficient to significantly improve the condition, but will not have serious side effects. Generally, the pharmaceutical composition contains 1-2000 mg of the compound of the present invention per dose, preferably, 5-200 mg the compound of the present invention per dose. Preferably, "one dose" is a capsule or tablet.

"Pharmaceutically acceptable carrier" means one or more compatible solid or liquid fillers or gelatinous materials which are suitable for human use and should be of sufficient purity and sufficiently low toxicity. "Compatible" herein means that each component in the composition can be well blended with a compound of the present invention and with each other between them, without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation of administration mode for the compound or pharmaceutical compositions of the present invention, and the representative administration mode includes (but is not limited to): oral, intratumoral, rectal, parenteral (intravenous, intramuscular or subcutaneous), and topical administration.

Solid dosage forms for oral administration include capsules, tablets, pills, powders and granules. In these solid dosage forms, the active compounds are mixed with at least one conventional inert excipient (or carrier), such as sodium citrate or dicalcium phosphate, or mixed with any of the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and arabic gum; (c) humectant, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffering agents.

The solid dosage forms, such as tablets, sugar pills, capsules, pills and granules, can be prepared by using coating and shell materials, such as enteric coatings and any other materials known in the art. They can contain an opaque agent and the release of the active compounds or compounds in the compositions can be released in a delayed mode in a given portion of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

The dosage forms for topical administration of compounds of the present invention include ointments, powders, patches, aerosol, and inhalants. The active ingredients are mixed with physiologically acceptable carriers and any preservatives, buffers, or propellant if necessary, under sterile conditions.

Compounds of the present invention can be administrated alone, or in combination with any other pharmaceutically acceptable compounds.

When the pharmaceutical compositions are used, a safe and effective amount of compound of the present invention is applied to a mammal (such as human) in need of, in which the dose of administration is a pharmaceutically effective dose. For a person weighed 60 kg, the daily dose is usually 1-2000 mg, preferably 5-500 mg. Of course, the particular dose should also depend on various factors, such as the route of administration, the healthy condition of patient, which are well within the skills of an experienced physician.

The main advantages of the invention include:

1. compounds of formula I are provided.

2. a novel ALK inhibitor and degradation agent, the preparation thereof and the application thereof are provided.

The inhibitor and degradation agent can inhibit the activity of ALK and degrade ALK at very low concentrations.

3. a pharmaceutical composition for treating diseases related to ALK activity is provided.

The present invention will be further illustrated below with reference to the specific examples. It should be understood that these examples are only to illustrate the invention but not to limit the disclosure of the invention. The experimental methods without specific conditions in the following embodiments are generally carried out according to conventional conditions, or in accordance with the conditions recommended by the manufacturer. The biological materials involved in the embodiments of the present invention can be obtained from commercially available channels, unless otherwise specified. Unless stated otherwise, percentages and parts are percentages by weight and parts by weight.

Example 1 Preparation of Compound (3)

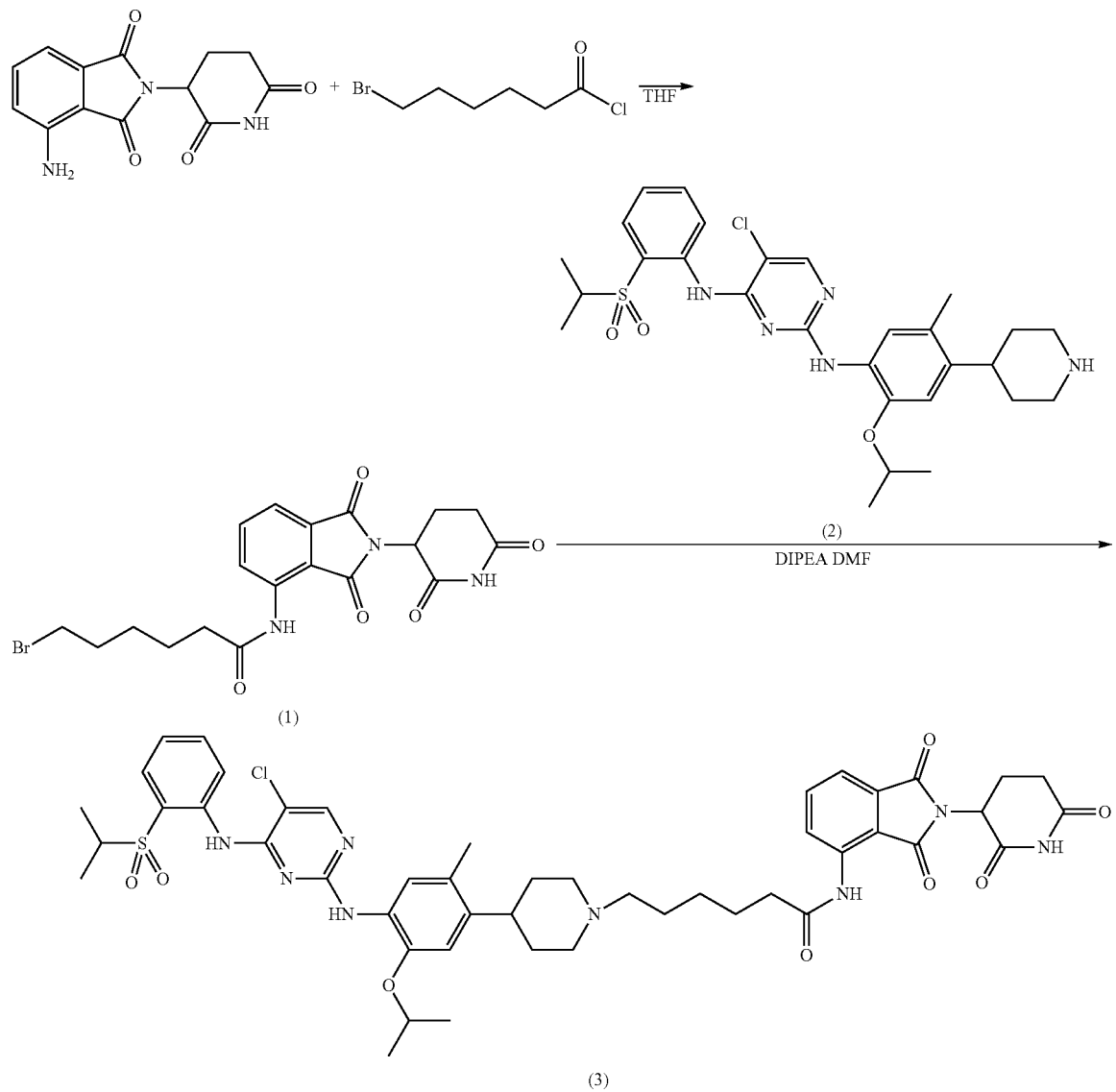

Step 1:

2.14 g of 6-bromohexanoyl chloride and 1.37 g of pomalidomide were dissolved in 50 ml of THF (tetrahydrofuran), and the mixture was stirred at reflux for 8 h. Then the solvent was removed under reduced pressure and the residue was purified by column chromatography to obtain 1.22 g of compound (1). MS (ESI): 450 [M+H]$^+$.

Step 2:

250 mg of compound (1), 365 mg of compound (2) and 650 mg of diisopropylethylamine were dissolved in 5 ml of N, N-dimethylformamide. The mixture was stirred at 80° C. for 6 h, and then cooled to room temperature. After concentration, the residue was purified by column chromatography to obtain 350 mg of compound (3) with a yield of 68.0%. MS (ESI): 927 [M+H]$^+$. $^1$H NMR (400 MHz, CDCl3) δ 9.49 (s, 1H), 8.28 (d, J=8.4 Hz, 1H), 8.15 (s, 1H), 7.98 (s, 1H), 7.95 (dd, J=8.0, 1.6 Hz, 1H), 7.87 (d, J=7.2 Hz, 1H), 7.79 (dd, J=8.4, 7.6 Hz, 1H), 7.62 (m, 1H), 7.60 (s, 1H), 7.25 (m, 1H), 6.92 (d, J=8.4 Hz, 1H), 6.82 (s, 1H), 6.52 (t, J=5.6 Hz, 1H), 4.89 (dd, J=11.6, 4.8 Hz, 1H), 4.48 (m, 1H), 3.25 (m, 1H), 2.66-2.91 (m, 6H), 2.52 (t, J=7.2 Hz, 2H), 2.11 (s, 3H), 2.10-2.45 (m, 6H), 1.71-1.90 (m, 4H), 1.40-1.65 (m, 6H), 1.34 (d, J=5.6 Hz, 6H), 1.31 (d, J=7.2 Hz, 6H).
Example 2 Preparation of Compound (7)
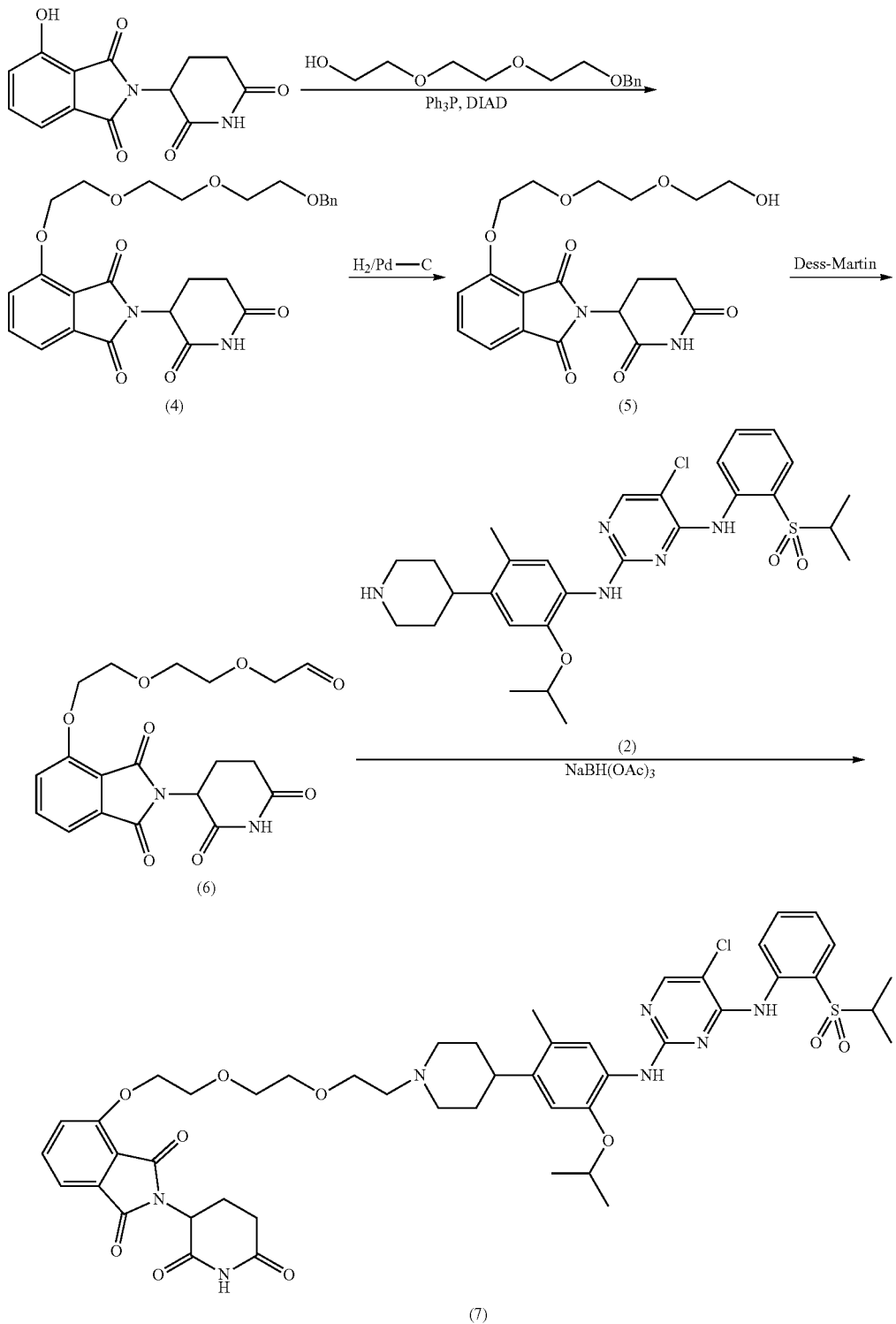

Step 1:

100 mg of 4-hydroxythalidomide, 96 mg of triethylene glycol monobenzyl ether, and 100 mg of triphenylphosphine were dissolved in 10 ml of anhydrous THF, and then 95 mg of DIAD (diisopropyl azodicarboxylate) was added dropwise. The reaction was carried out at room temperature for 2 h. THF was removed under reduced pressure, and 110 mg of compound (4) was obtained after purification by column chromatography. MS (ESI): 497 [M+H]$^+$.

Step 2:

100 mg of compound (4) and 100 mg of 10% Pd—C were added into 10 ml of methanol and the mixture was hydrogenated at room temperature overnight. Then the mixture was filtered and the filtrate was concentrated. The residue was purified by column chromatography to obtain 40 mg of compound (5). MS (ESI): 407 [M+H]$^+$.

Step 3:

30 mg of compound (5) was dissolved in 5 ml of dichloromethane, then 47 mg of Dess-martin oxidant was added. The mixture was reacted at room temperature for 3 h. To the reaction system were added a saturated aqueous solution of NaHCO$_3$ and a saturated aqueous solution of Na$_2$S$_2$O$_3$, and stirred for 5 min. The organic layer was separated, dried over anhydrous Na$_2$S$_2$O$_3$, and concentrated to dryness. The obtained compound (6) was directly used in the next step.

After compound (6) was dissolved in 7 ml of dichloromethane, 45 mg of raw material (2) and 23 mg of NaBH(OAc)$_3$ were added, and the mixture was reacted overnight at room temperature. Dichloromethane was distilled off under reduced pressure. 37 mg of compound (7) was obtained after purification by column chromatography. 946 [M+H]$^+$. $^1$H NMR (500 MHz, CDCl$_3$) δ 9.49 (s, 1H), 8.58 (d, J=8.5 Hz, 1H), 8.15 (s, 1H), 7.98 (s, 1H), 7.92 (d, J=7.5 Hz, 1H), 7.60-7.69 (m, 2H), 7.56 (s, 1H), 7.47 (d, J=7.5 Hz, 1H), 7.24-7.27 (m, 2H), 6.81 (s, 1H), 4.93 (dd, J=12.0, 5.0 Hz, 1H), 4.53 (m, 1H), 4.35 (t, J=4.2 Hz, 2H), 3.95 (t, J=4.8 Hz, 2H), 3.81 (m, 2H), 3.70 (br, 2H), 3.67 (m, 2H), 3.26 (m, 1H), 3.18 (br, 2H), 2.65-2.90(m, 61-I), 2.11 (s, 3H), 2.10-2.32 (m, 4H), 1.70-1.91 (m, 4H), 1.35 (d, J=5.5 Hz, 6H), 1.32 (d, J=7.0 Hz, 6H).

Example 3 Preparation of Compound (10)

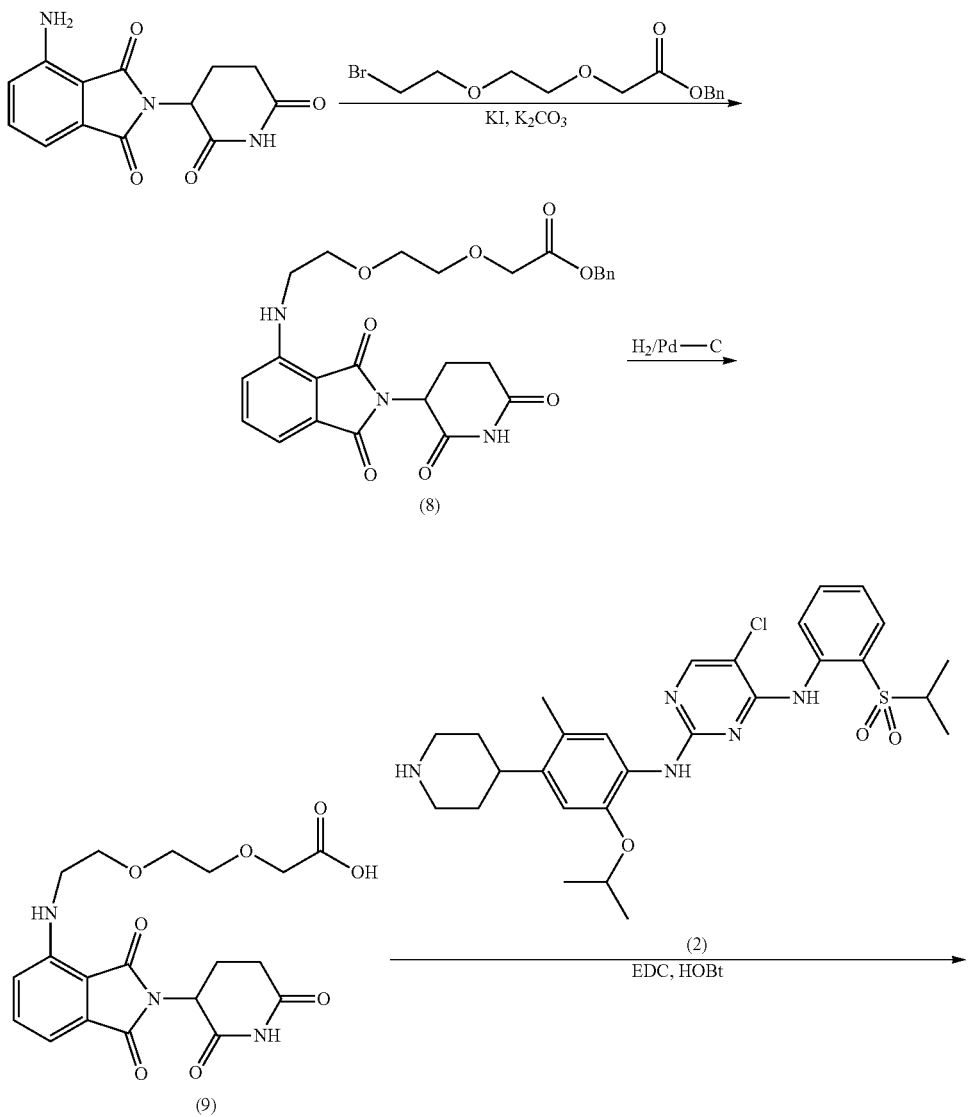

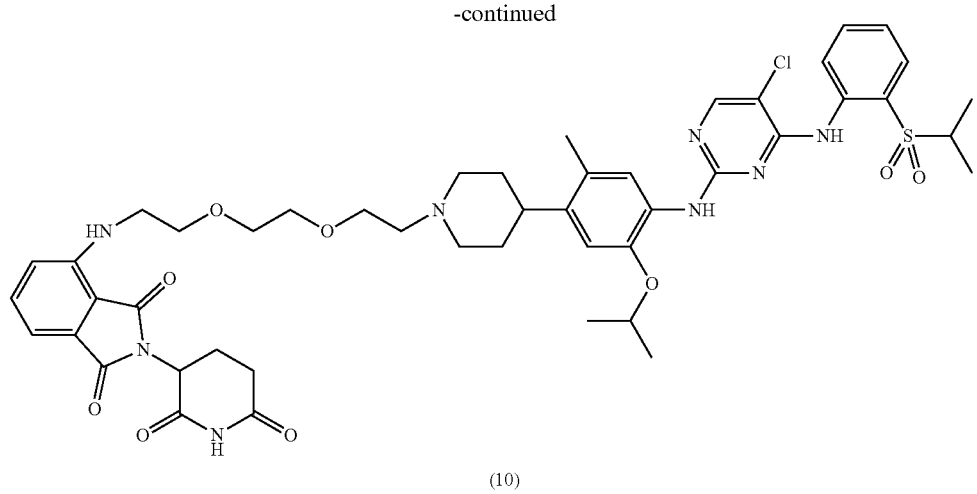

(10)

Step 1:

174 mg of benzyl 2-(2-(2-bromoethoxy)ethoxy)acetate, 100 mg of potassium carbonate, 20 mg of potassium iodide and 100 mg of pomalidomide were added into 20 ml of DMF (N, N-dimethylformamide), and reacted at 80° C. overnight. The reaction solution was purified by column chromatography to obtain 113 mg of compound (8). MS (ESI): 510 [M+H]⁺.

Step 2:

100 mg of compound (8) and 100 mg of 10% Pd—C were added into 10 ml of methanol and the mixture was hydrogenated at room temperature overnight. Then the mixture was filtered and the filtrate was concentrated. The residue was purified by column chromatography to obtain 73 mg of compound (9). MS (ESI anion): 418 [M−H]⁻.

Step 3:

50 mg of compound (9) and 50 mg of raw material (2) were dissolved in 5 ml of dichloromethane, and 20 mg of HOBt (1-hydroxybenzotriazole) and 40 mg of EDC (1-(3-dimethylaminopropyl)-3-ethyl-carbodiimide hydrochloride) were added. The mixture was reacted at room temperature overnight. Dichloromethane was distilled off under reduced pressure, and 45 mg of compound (10) was obtained after purification by column chromatography. $^1$H NMR (400 MHz, CDCl$_3$) δ 9.49 (s, 1H), 8.58 (d, J=8.4 Hz, 1H), 8.15(s, 1H), 7.98 (s, 1H), 7.98 (s, 1H), 7.92 (dd, J=8.0, 1.6 Hz, 1H), 7.62 (m, 1H), 7.56 (s, 1H), 7.49 (dd, J=8.4, 7.6 Hz, 1H), 7.25 (m, 1H), 7.11 (d, J=7.2 Hz, 1H), 6.92 (d, J=8.4 Hz, 1H), 6.82 (s, 1H), 6.52 (t, J=5.6 Hz, 1H), 4.90 (dd, J=12.0, 5.6 Hz, 1H), 4.67 (s, 2H), 4.54 (m, 1H), 3.73 (m, 4H), 3.47 (m, 2H), 3.26 (m, 1H), 3.19 (br, 2H), 2.63-2.89 (m, 6H), 2.14 (s, 3H), 2.08-2.30 (m, 3H), 1.71-1.92 (m, 4H), 1.35 (d, J=6.0 Hz, 6H), 1.32 (d, J=6.8 Hz, 6H).

Example 4 Preparation of Compound (13)

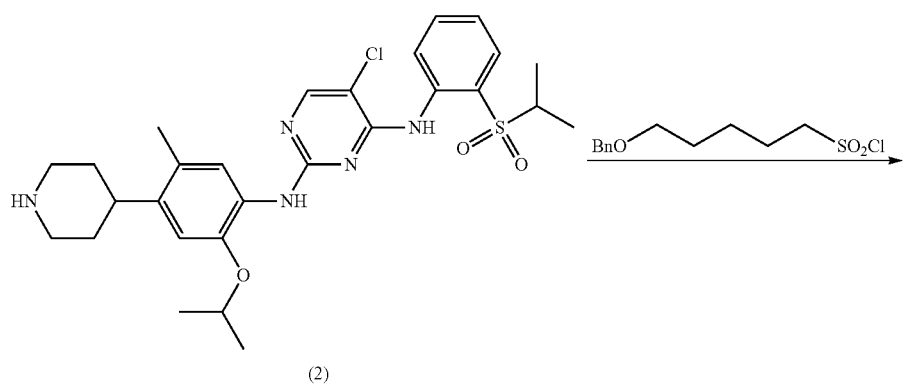

(2)

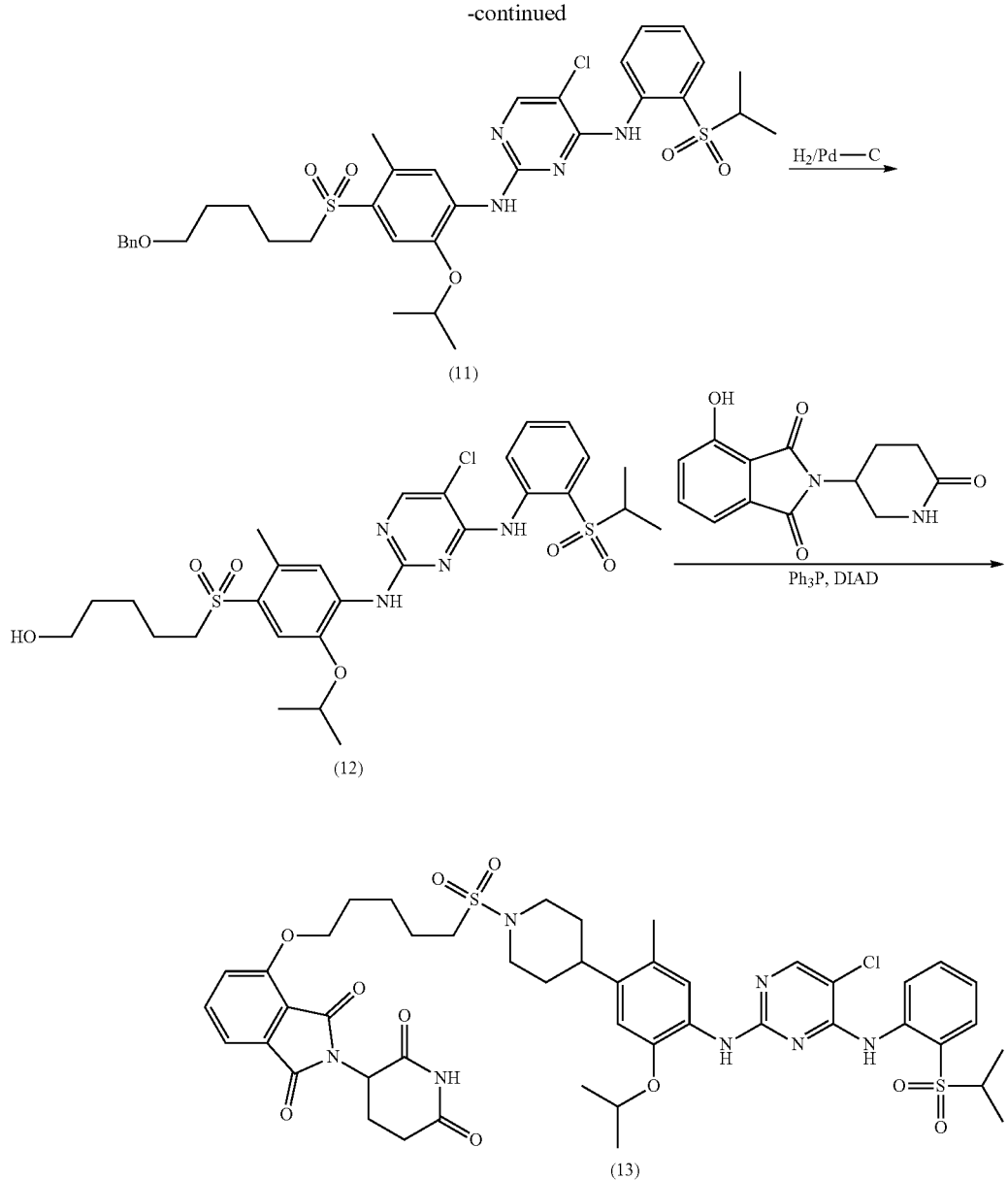

Step 1:

200 mg of raw material (2) was dissolved in 10 ml of dichloromethane, 100 mg of triethylamine and 200 mg of 5-benzyloxypentanesulfonyl chloride were added, and the mixture was reacted at room temperature overnight. The dichloromethane was distilled off under reduced pressure and 267 mg of compound (11) was obtained after purification by column chromatography. MS (ESI): 798 [M+H]+.

Step 2:

200 mg of compound (11) was added into 20 ml of methanol and 200 mg of 10% Pd—C, the gas was changed 3 times with $H_2$, and the mixture was reacted at room temperature overnight. Then the mixture was filtered and the filtrate was concentrated. The residue was purified by column chromatography to obtain 154 mg of compound (12). MS (ESI): 708 [M+H]+.

Step 3:

100 mg of 4-hydroxythalidomide, 100 mg of triphenylphosphine and 150 mg of compound (12) were dissolved in 30 ml of anhydrous tetrahydrofuran, 100 mg of DIAD (diisopropyl azodicarboxylate) was added dropwise, and the reaction was carried out at room temperature for 3 h. Tetrahydrofuran was removed under reduced pressure, and 75 mg of compound (13) was obtained after purification by column chromatography. MS (ESI): 964 [M+H]+. $^1$H NMR (400 MHz, $CDCl_3$) δ 9.48 (s, 1H), 8.58(d, J=8.4 Hz, 1H), 8.15 (s, 1H), 7.98 (s, 1H), 7.92 (d, J=7.5 Hz, 1H), 7.60-7.69 (m, 2H), 7.56 (s, 1H), 7.47 (d, J=7.5 Hz, 1H), 7.24-7.27 (m, 1H), 6.81 (s, 1H), 4.90(dd, J=12.0, 4.4 Hz, 1H), 4.48(m, 1H), 3.55(t, J=7.2 Hz, 2H), 3.25-3.34(m, 3H), 2.66-2.91(m, 5H), 2.11 (s, 3H), 2.10-2.46 (m, 4H), 1.71-1.90 (m, 4H), 1.40-1.65 (m, 6H), 1.35 (d, J=5.6 Hz, 6H), 1.31 (d, J=7.2 Hz, 6H).

Similarly, the following compounds were prepared by a method similar to the above example:

| Compound No. | Structure of compound | Reference example for synthesis method | MS(ESI) |
| --- | --- | --- | --- |
| 114 | | 2, 3 | 989[M + H]⁺ |
| 115 | | 2 | 990[M + H]⁺ |

| Compound No. | Structure of compound | Reference example for synthesis method | MS(ESI) |
|---|---|---|---|
| 16 | 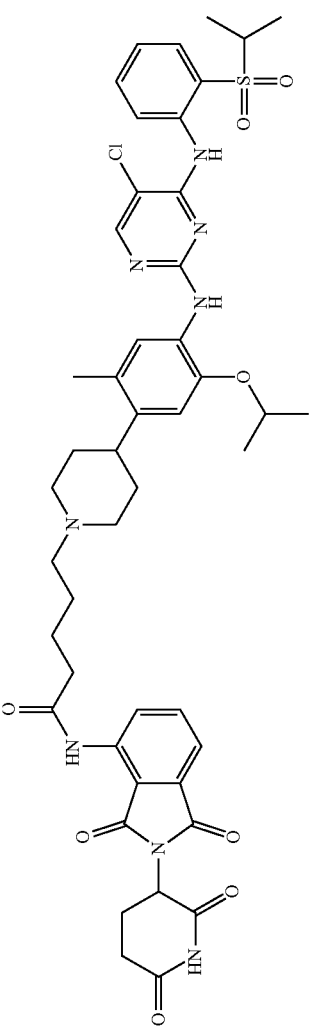 | 1 | 913[M + H]+ |
| 17 | 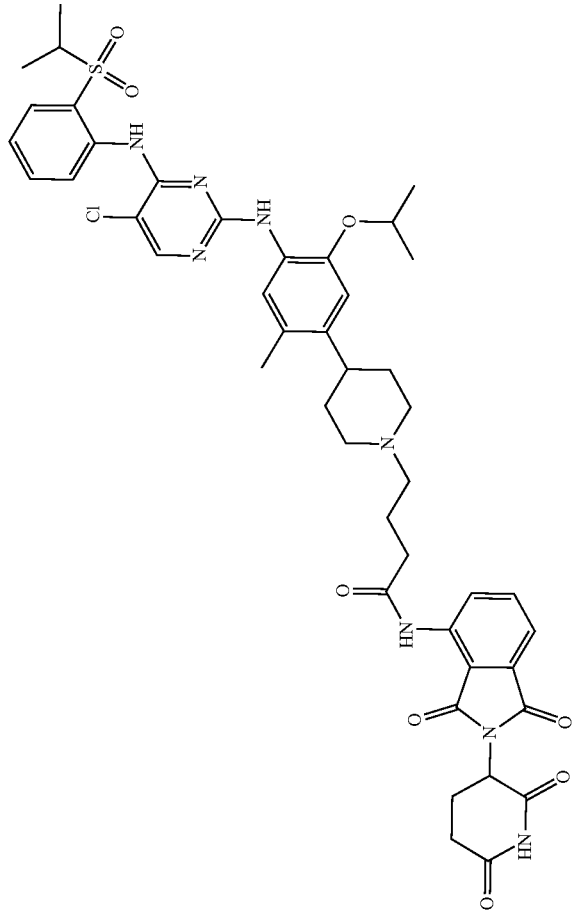 | 1 | 899[M + H]+ |

-continued
| Compound No. | Structure of compound | Reference example for synthesis method | MS(ESI) |
|---|---|---|---|
| 18 | 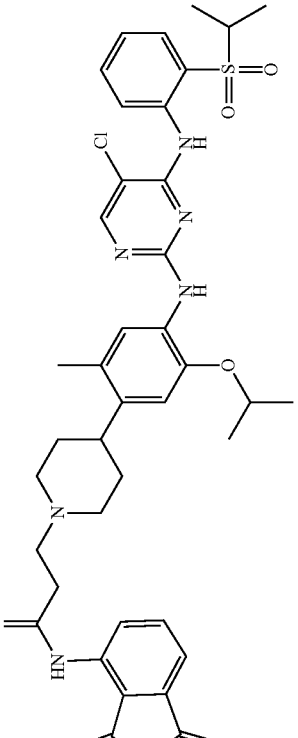 | 1 | 885[M + H]⁺ |
| 19 | 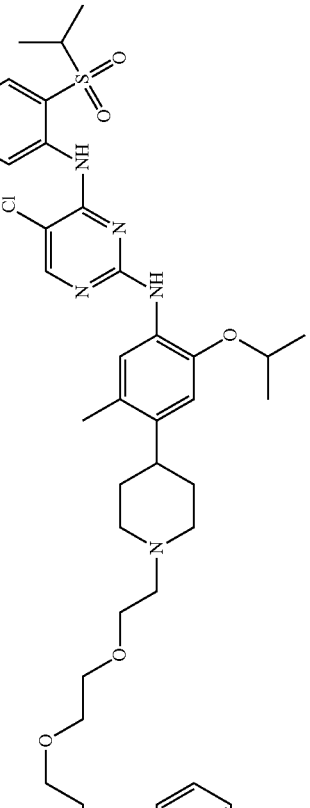 | 1 | 973[M + H]⁺ |

-continued

| Compound No. | Structure of compound | Reference example for synthesis method | MS(ESI) |
|---|---|---|---|
| 20 | | 1 | 1017[M + H]⁺ |
| 21 | | 2 | 902[M + H]⁺ |

-continued

| Compound No. | Structure of compound | Reference example for synthesis method | MS(ESI) |
|---|---|---|---|
| 22 | (structure) | 2 | 900[M + H]⁺ |
| 23 | (structure) | 2 | 886[M + H]⁺ |

-continued

| Compound No. | Structure of compound | Reference example for synthesis method | MS(ESI) |
|---|---|---|---|
| 24 | | 2 | 872[M + H]⁺ |
| 25 | | 2 | 1034[M + H]⁺ |

| Compound No. | Structure of compound | Reference example for synthesis method | MS(ESI) |
|---|---|---|---|
| 26 | | 2 | 1078[M + H]⁺ |
| 27 | | 2, 3 | 901[M + H]⁺ |

-continued
| Compound No. | Structure of compound | Reference example for synthesis method | MS(ESI) |
|---|---|---|---|
| 28 | 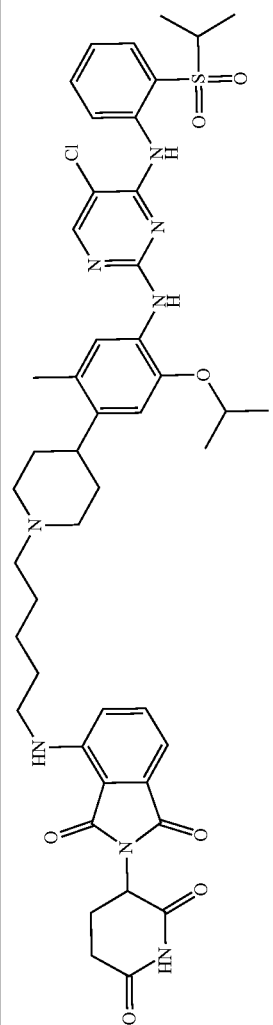 | 2, 3 | 899[M + H]+ |
| 29 | 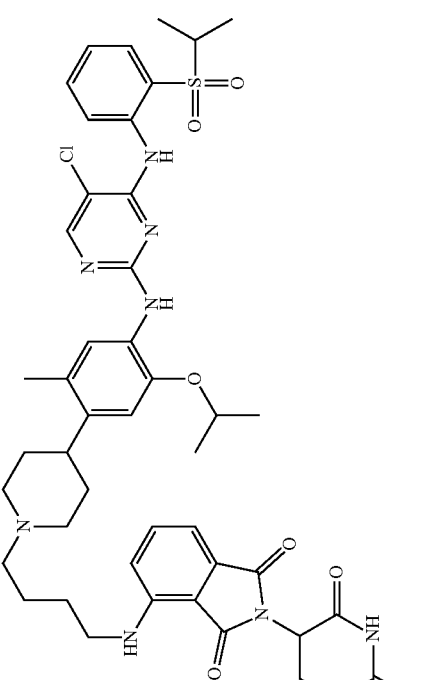 | 2, 3 | 885[M + H]+ |

-continued

| Compound No. | Structure of compound | Reference example for synthesis method | MS(ESI) |
|---|---|---|---|
| 30 | | 2, 3 | 871[M + H]+ |
| 31 | | 2, 3 | 1033[M + H]+ |

-continued

| Compound No. | Structure of compound | Reference example for synthesis method | MS(ESI) |
|---|---|---|---|
| 32 | | 2, 3 | 1077[M + H]⁺ |
| 33 | | 2, 3 | 914[M + H]⁺ |

-continued
| Compound No. | Structure of compound | Reference example for synthesis method | MS(ESI) |
|---|---|---|---|
| 34 | 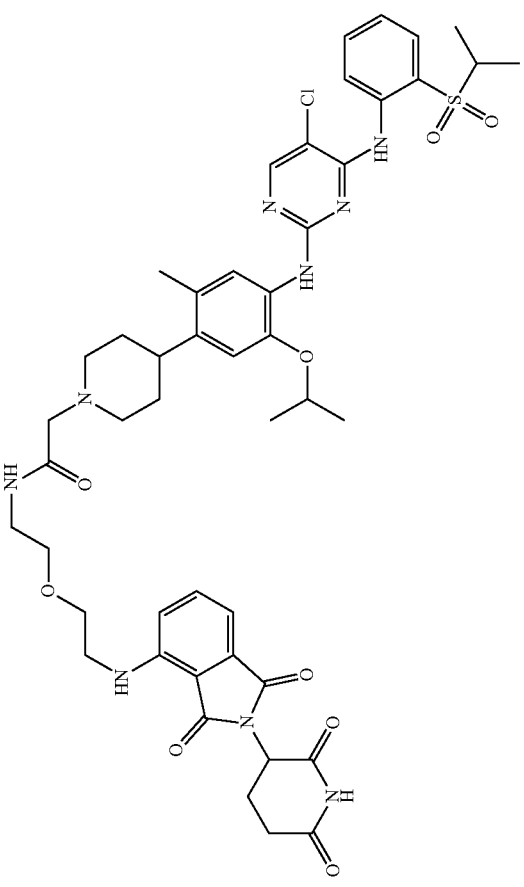 | 2, 3 | 958[M + H]+ |
| 35 | 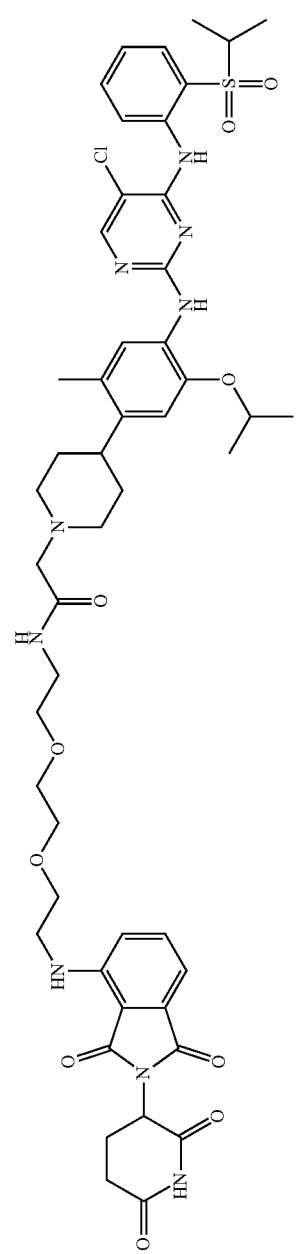 | 2, 3 | 1002[M + H]+ |

| Compound No. | Structure of compound | Reference example for synthesis method | MS(ESI) |
|---|---|---|---|
| 36 | 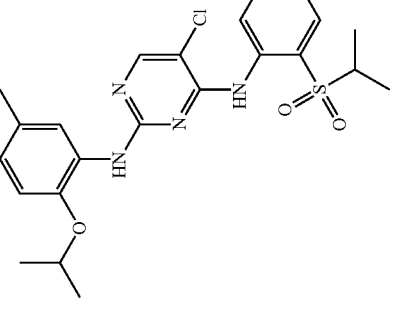 | 2, 3 | 1046[M + H]+ |
| 37 | 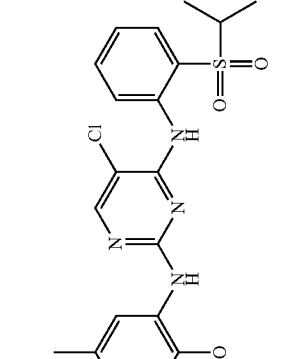 | 2, 3 | 1090[M + H]+ |

-continued

| Compound No. | Structure of compound | Reference example for synthesis method | MS(ESI) |
|---|---|---|---|
| 38 | (structure) | 2, 3 | 1134[M + H]+ |
| 39 | (structure) | 2 | 915[M + H]+ |

| Compound No. | Structure of compound | Reference example for synthesis method | MS(ESI) |
|---|---|---|---|
| 40 | 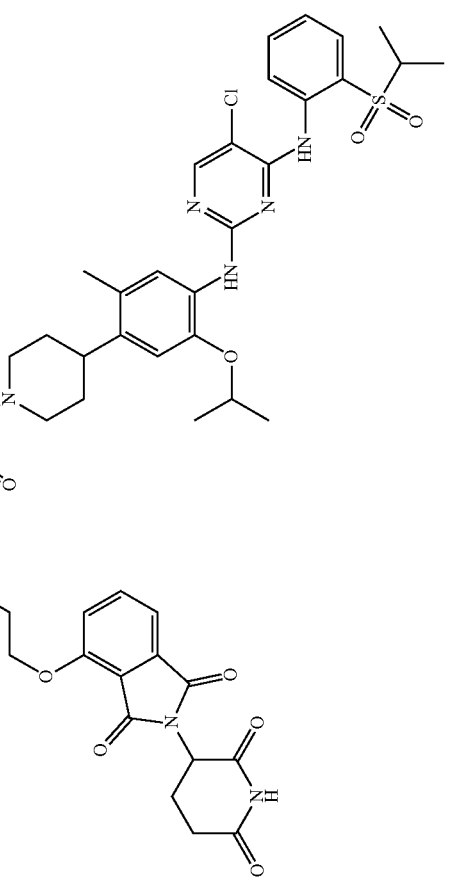 | 2 | 959[M + H]+ |
| 41 | 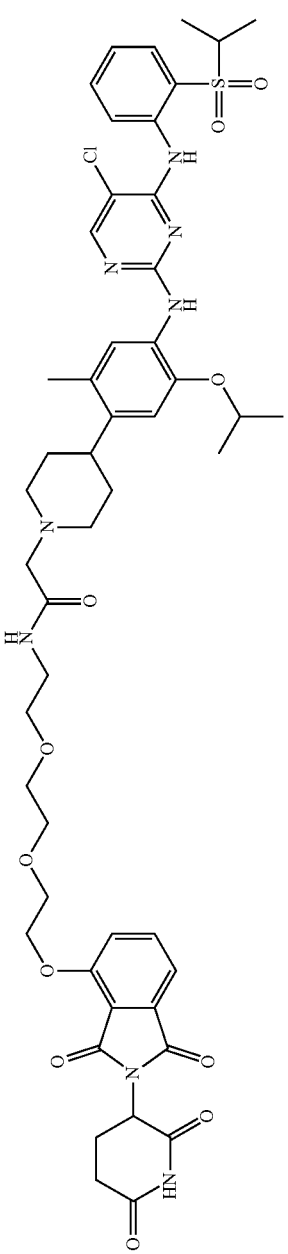 | 2 | 1003[M + H]+ |

| Compound No. | Structure of compound | Reference example for synthesis method | MS(ESI) |
|---|---|---|---|
| 42 | 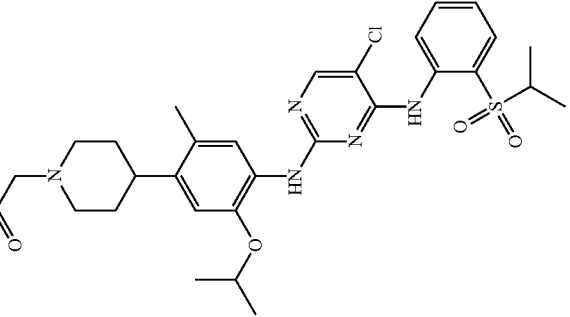 | 2 | 1047[M + H]+ |
| 43 | 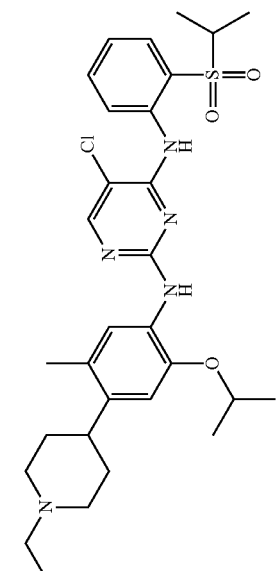 | 2 | 1091[M + H]+ |

| Compound No. | Structure of compound | Reference example for synthesis method | MS(ESI) |
|---|---|---|---|
| 44 | 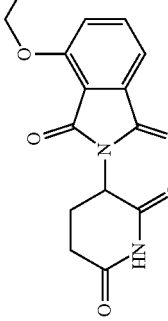 | 2 | 1135[M + H]+ |

| Compound No. | Structure of compound | Reference example for synthesis method | MS(ESI) |
|---|---|---|---|
| 45 | 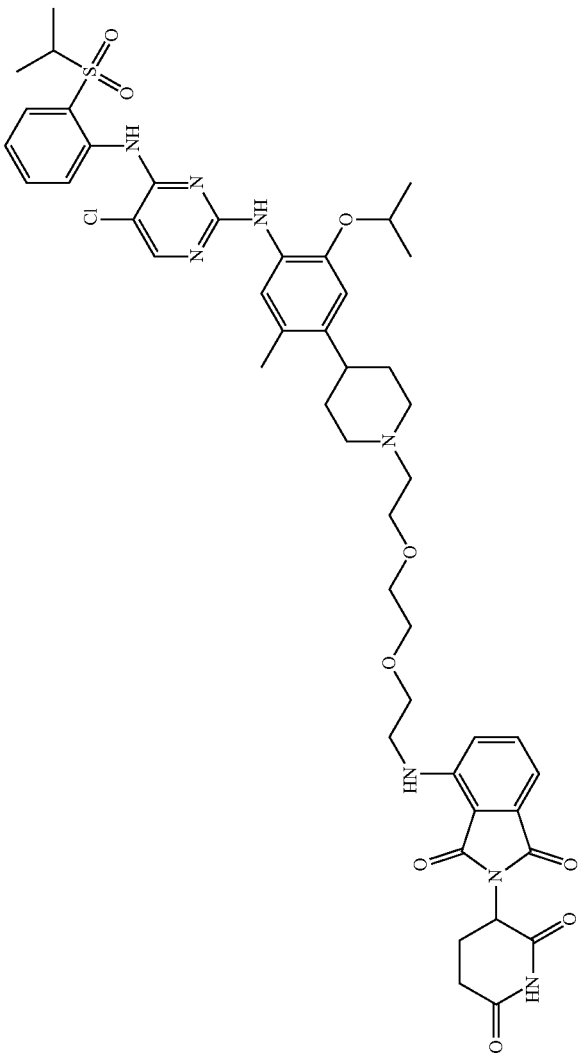 | 2, 3 | 945[M + H]+ |

Example 5 Testing the ALK Inhibition Activity of Compound by Caliper Assay

The experimental steps were as follows:
Preparation of 1×kinase reaction buffer (50 mM HEPES, PH 7.5; 0.0015% Brij-35) and kinase reaction termination solution (100 mM HEPES, PH 7.5; 0.0015% Brij-35; 0.2% Coating Reagent; 50 mM EDTA);
Preparation of experimental samples: 100 µl of 5 µM sample solution (dissolved in 100% DMSO) was added to a 96-well plate to obtain a 50×sample solution. As controls, two wells containing only 100 µL of 100% DMSO were set on the same plate. One was served as a control without samples and the other was served as a control without enzymes. 10 µL of sample and 90 µL, of 1×kinase reaction buffer were added to a 96-well plate as a transfer plate. The transfer plate was shaken for 10 minutes.
Preparation of the test plate: taking 5 µL of each of the prepared samples from the 96-well transfer plate into a 384-well plate.
Kinase reaction: to 5 µL of 5×compound solution (dissolved in DMSO, diluted 10 times with water) was added 10 µL of 2.5×ALK kinase solution (kinase was diluted with 1×kinase reaction buffer), which was incubated at room temperature for 10 min, and then 10 µL of 2.5×substrate peptide solution (FAM-labeled peptide and ATP were diluted with 1×kinase reaction buffer) was added.
Termination of the kinase reaction: 25 µL of kinase reaction termination solution was added after being reacted at 28° C. for a period of time.
The fluorescence (F) was tested on a Caliper and data was collected.
The inhibition rate of kinase activity was calculated: the percent inhibition rate of kinase activity=$(F_{DMSO\ control}-F_{sample})/(F_{DMSO\ control}-F_{negative\ control}) \times 100$, with DMSO as the solution control, and no kinase as the negative control.
The results show that the inhibitory activity of compound (100 nM) on ALK is shown in the following table:

| Compound No. | Inhibition(%) |
|---|---|
| 3 | 98% |
| 7 | 97% |
| 10 | 99% |
| 13 | 69% |
| 14 | 89% |
| 15 | 95% |
| 45 | 98% |

Example 6 Testing the ALK Protein Degradation Activity of Compound by Western Blot Cell lines: H2228 cell lines (human non-small cell line lung cancer cells, available from ATCC) were cultured in RPMI1640 medium containing 10% calf serum in a 37° C., 5% $CO_2$, and saturated humidity incubator.
DMSO control group and compound intervention group (10 µM) were set. Cells were collected after the treatment for 24 hours, then 100 µL of pre-chilled cell lysate was added and cells were lysed on ice for 30 minutes. Total cell protein was extracted, and protein concentration was determined and quantified by diquinolinecarboxylic acid (BCA) method. After routine gelatinization, loading, electrophoresis, then transferring to membrane and blocking, mouse anti-human ALK (1:1000) was added respectively, and incubated at 4° C. overnight. The mixture was rinsed and then horseradish peroxidase labeled goat anti-rabbit IgG (1:5000) was added. After the rinsing it was developed by the ECL developing solution, the Bio-Rad gel imaging system was used for scanning and imaging, and the computer software was used for analysis. Glycerol phosphate dehydrogenase (GAPDH) was used as an internal control.
Image J software was used to analyze the gray scale of each band to calculate the degradation rate of the compound to degrade ALK protein.
The results show that the degradation activity of the compound (1 µM) on ALK protein in 112228 cells is shown in the following table:

| Compound No. | ALK degradation activity |
|---|---|
| 3 | ++++ |
| 7 | ++++ |
| 10 | ++++ |
| 13 | ++++ |
| 14 | ++++ |
| 15 | ++++ |
| 16 | ++++ |
| 17 | ++++ |
| 18 | ++++ |
| 19 | ++++ |
| 20 | ++++ |
| 21 | +++ |
| 22 | +++ |
| 23 | +++ |
| 24 | +++ |
| 25 | ++++ |
| 26 | +++ |
| 27 | ++++ |
| 28 | ++++ |
| 29 | +++ |
| 30 | +++ |
| 31 | ++++ |
| 32 | +++ |
| 33 | ++++ |
| 34 | ++++ |
| 35 | ++++ |
| 36 | ++++ |
| 37 | +++ |
| 38 | +++ |
| 39 | ++++ |
| 40 | ++++ |
| 41 | ++++ |
| 42 | ++++ |
| 43 | +++ |
| 44 | +++ |
| 45 | ++++ |

Note:
In the above table,
"−" represents no degradation activity,
"+" represents a degradation rate of 10%-30%,
"++" represents a degradation rate of 30%-50%, and
"+++" represents a degradation rate of 50%-90%, and
"++++" means the degradation rate is greater than 90%.

Example 7 Testing the Inhibitory Effect of Formula Compound on the Proliferation of SU-DHL-1 Cells by CTG Assay The inhibitory effect of the compound on the proliferation of SU-DHL-1 cells (B lymphoma cells) was determined by the CCK8 method in vitro. The Cells were cultured and the compound was prepared referring to the method of Example 7, and the culture time after administration was 72 hours. Subsequently, an appropriate amount of CTG reagent was added, the luminescence value was measured, and the inhibition rate was calculated.
The inhibitory effect of the synthesized compound (100 µM) on the proliferation of SU-DHL-1 cells in vitro is shown in the table below:

| Compound No. | Inhibition(%) |
|---|---|
| 3 | 72 |
| 7 | 98 |
| 14 | 99 |
| 15 | 100 |
| 45 | 97 |

The above result shows that the synthesized compounds of formula I have good inhibitory activity on the proliferation of SU-DHL-1 cells.

All publications mentioned herein are incorporated by reference as if each individual document is cited as a reference, as in the present application. It should also be understood that, after reading the above teachings of the present invention, those skilled in the art can make various changes or modifications, equivalents of which falls in the scope of claims as defined in the appended claims.

What is claimed:

1. A compound represented by the following formula I, or a pharmaceutically acceptable salt thereof:

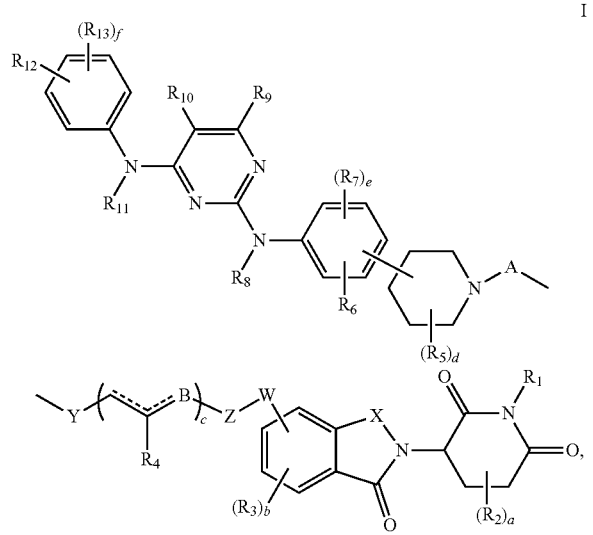

I wherein
— is a single bond;
═ is a single or a double bond;
A is missing a bond, C(═O)X1, or substituted or unsubstituted $C_{1-8}$ hydrocarbyl group, wherein X1 is a bond or $(CR_{35}R_{36})_kO$, wherein $R_{35}$ and $R_{36}$ are each independently selected from the group consisting of H and substituted or unsubstituted $C_{1-8}$ hydrocarbyl group, and k is an integer between 0 and 3;
W is a bond, O, or $NR_{17}$, wherein $R_{17}$ is H or substituted or unsubstituted $C_{1-8}$ hydrocarbyl group;
Y is $(CR_{22}R_{23})_h$, wherein h is an integer between 0 and 30, and $R_{22}$ and $R_{23}$ are each independently selected from the group consisting of H, cyano, hydroxyl, amino, and substituted and unsubstituted $C_{1-8}$ hydrocarbyl group;
Z is $(CR_{24}R_{25})_i$, wherein i is an integer between 0 and 30, and $R_{24}$ and $R_{25}$ are each independently selected from the group consisting of H, cyano, hydroxyl, amino, and substituted or unsubstituted $C_{1-8}$ hydrocarbyl group;
B is O;
X is $CH_2$; or C(═O);

$R_1$ is selected from the group consisting of H, substituted or unsubstituted $C_{1-8}$ hydrocarbyl group, substituted or unsubstituted $C_{1-8}$ cyclic hydrocarbyl group, substituted or unsubstituted $C_{1-8}$ heterocyclic hydrocarbyl group, and substituted or unsubstituted $C_{1-6}$ acyl group;
$R_8$ is selected from the group consisting of H, substituted or unsubstituted $C_{1-8}$ hydrocarbyl group, substituted or unsubstituted $C_{1-8}$ cyclic hydrocarbyl group, substituted or unsubstituted $C_{1-8}$ heterocyclic hydrocarbyl group, and substituted or unsubstituted $C_{1-6}$ acyl group;
$R_{11}$ is selected from the group consisting of H, substituted or unsubstituted $C_{1-8}$ hydrocarbyl group, substituted or unsubstituted $C_{1-8}$ cyclic hydrocarbyl group, substituted or unsubstituted $C_{1-8}$ heterocyclic hydrocarbyl group and substituted or unsubstituted $C_{1-6}$ acyl group;
$R_2$ is selected from the group consisting of hydrogen, $OR_{26}$, $NR_{27}R_{28}$, cyano, halogen, substituted or unsubstituted $C_{1-8}$ hydrocarbyl group, substituted or unsubstituted $C_{1-8}$ cyclic hydrocarbyl group, substituted or unsubstituted $C_{1-8}$ heterocyclic hydrocarbyl group, substituted or unsubstituted $C_{1-6}$ acyl group, and substituted or unsubstituted $C_{1-6}$ amido group, wherein $R_{26}$, $R_{27}$, and $R_{28}$ are each independently selected from the group consisting of H and substituted or unsubstituted $C_{1-8}$ hydrocarbyl group;
$R_5$ is selected from the group consisting of hydrogen, $OR_{26}$, $NR_{27}R_{28}$, cyano, halogen, substituted or unsubstituted $C_{1-8}$ hydrocarbyl group, substituted or unsubstituted $C_{1-8}$ cyclic hydrocarbyl group, substituted or unsubstituted $C_{1-8}$ heterocyclic hydrocarbyl group, substituted or unsubstituted $C_{1-6}$ acyl group, and substituted or unsubstituted $C_{1-6}$ amido group, wherein $R_{26}$, $R_{27}$, and $R_{28}$ are each independently selected from the group consisting of H and substituted or unsubstituted $C_{1-8}$ hydrocarbyl group;
$R_3$ is selected from the group consisting of H, $OR_{29}$, $NR_{30}R_{31}$, cyano, halogen, nitro, substituted or unsubstituted $C_{1-8}$ hydrocarbyl group, substituted or unsubstituted cyclic hydrocarbyl group, and substituted or unsubstituted heterocyclic hydrocarbyl group, wherein $R_{29}$, $R_{30}$, and $R_{31}$ are each independently selected from the group consisting of H and substituted or unsubstituted $C_{1-8}$ hydrocarbyl group;
$R_6$ is selected from the group consisting of H, $OR_{29}$, $NR_{30}R_{31}$, cyano, halogen, nitro, substituted or unsubstituted $C_{1-8}$ hydrocarbyl group, substituted or unsubstituted cyclic hydrocarbyl group, and unsubstituted heterocyclic hydrocarbyl group; wherein $R_{29}$, $R_{30}$, and $R_{31}$ are each independently selected from the group consisting of H and substituted or unsubstituted $C_{1-8}$ hydrocarbyl group;
$R_7$ is selected from the group consisting of H, $OR_{29}$, $NR_{30}R_{31}$, cyano, halogen, nitro, substituted or unsubstituted $C_{1-8}$ hydrocarbyl group, substituted or unsubstituted cyclic hydrocarbyl group, and substituted or unsubstituted heterocyclic hydrocarbyl group, wherein $R_{29}$, $R_{30}$, and $R_{31}$ are each independently selected from the group consisting of H and substituted or unsubstituted $C_{1-8}$ hydrocarbyl group;
$R_9$ is selected from the group consisting of H, $OR_{29}$, $NR_{30}R_{31}$, cyano, halogen, nitro, substituted or unsubstituted $C_{1-8}$ hydrocarbyl group, substituted or unsubstituted cyclic hydrocarbyl group, and substituted or unsubstituted heterocyclic hydrocarbyl group, wherein $R_{29}$, $R_{30}$, and $R_{31}$ are each independently selected from the group consisting of H and substituted or unsubstituted $C_{1-8}$ hydrocarbyl group;
$R_{10}$ is selected from the group consisting of H, $OR_{29}$, $NR_{30}R_{31}$, cyano, halogen, nitro, substituted or unsubstituted $C_{1-8}$ hydrocarbyl group, substituted or unsubstituted cyclic hydrocarbyl group, and substituted or unsubstituted heterocyclic hydrocarbyl group, wherein $R_{29}$, $R_{30}$, and $R_{31}$ are each independently selected from the group consisting of H and substituted or unsubstituted $C_{1-8}$ hydrocarbyl group;

$R_{12}$ is selected from the group consisting of H, $OR_{29}$, $NR_{30}R_{31}$, cyano, halogen, nitro, substituted or unsubstituted $C_{1-8}$ hydrocarbyl group, substituted or unsubstituted cyclic hydrocarbyl group, substituted or unsubstituted heterocyclic hydrocarbyl group, $X6S(=O)_j R_{32}$, and $X6C(=O)R_{33}$, wherein j is an integer between 0 to 2, $R_{29}$, $R_{30}$, $R_{31}$, $R_{32}$, and $R_{33}$ are each independently selected from the group consisting of H and substituted or unsubstituted $C_{1-8}$ hydrocarbyl group, and X6 is a bond;

$R_{13}$ is selected from the group consisting of H, $OR_{29}$, $NR_{30}R_{31}$, cyano, halogen, nitro, substituted or unsubstituted $C_{1-8}$ hydrocarbyl group, substituted or unsubstituted cyclic hydrocarbyl group, and substituted or unsubstituted heterocyclic hydrocarbyl group, wherein $R_{29}$, $R_{30}$, and $R_{31}$ are each independently selected from the group consisting of H and substituted or unsubstituted $C_{1-8}$ hydrocarbyl group;

$R_4$ is selected from the group consisting of H, cyano, carboxyl, substituted or unsubstituted $C_{1-8}$ hydrocarbyl group, and substituted or unsubstituted $C_{1-8}$ hydrocarbyloxycarbonyl group;

a is an integer between 0 and 5;
b is an integer between 0 and 3;
c is an integer between 1 and 30;
d is an integer between 0 and 9;
e is an integer between 0 and 3;
f is an integer between 0 and 4; and wherein any of the substituents is selected from the group consisting of halogen, unsubstituted or halogenated C1-C6 alkyl, unsubstituted or halogenated C1-C6 alkoxy, unsubstituted or halogenated C2-C6 alkoxyalkyl, unsubstituted or halogenated C3-C8 cycloalkyl, unsubstituted or halogenated C2-C6 alkylcarbonyl, unsubstituted or halogenated C1-C6 alkylene-hydroxyl, and unsubstituted or C1-C6 alkyl substituted amine.

2. The compound according to claim 1, or a pharmaceutically acceptable salt thereof, wherein:
in formula I, A is a bond; W is a bond or O; Y is $(CR_{22}R_{23})_h$, wherein $R_{22}$ and $R_{23}$ are each independently selected from the group consisting of H, hydroxyl, and substituted or unsubstituted $C_{1-4}$ hydrocarbyl group, and h is an integer between 0 and 3; Z is $(CR_{24}R_{25})_i$, wherein $R_{24}$ and $R_{25}$ are each independently selected from the group consisting of H, hydroxyl, and substituted or unsubstituted $C_{1-4}$ hydrocarbyl group and i is an integer between 0 and 3; and c is an integer between 1 and 6; or in formula I, A is a bond; W is $NR_{17}$, wherein $R_{17}$ is H or substituted or unsubstituted $C_{1-4}$ hydrocarbyl group; Y is $(CR_{22}R_{23})_h$, wherein $R_{22}$ and $R_{23}$ are each independently selected from the group consisting of H, hydroxyl, and substituted or unsubstituted $C_{1-4}$ hydrocarbyl group, and h is an integer between 0 and 3; Z is $(CR_{24}R_{25})_i$, wherein $R_{24}$ and $R_{25}$ are each independently selected from the group consisting of H, hydroxyl, and substituted or unsubstituted and $C_{1-4}$ hydrocarbyl group, and i is an integer between 0 and 4; and c is an integer between 1 and 6; or in formula I, A is a bond; W is a bond; Y is $(CR_{22}R_{23})_h$, wherein $R_{22}$ and $R_{23}$ are each independently selected from the group consisting of H, hydroxyl, and substituted and unsubstituted $C_{1-4}$ hydrocarbyl group, and h is an integer between 0 and 3; Z is $(CR_{24}R_{25})_i$, wherein $R_{24}$, and $R_{25}$ are each independently selected from the group consisting of H, hydroxyl, and substituted or unsubstituted $C_{1-4}$ hydrocarbyl group, and i is an integer between 0 and 3; and c is an integer between 1 and 10.

3. The compound according to claim 1, or a pharmaceutically acceptable salt thereof, wherein in formula I, X is $C(=O)$.

4. The compound according to claim 1, or a pharmaceutically acceptable salt thereof, wherein $R_{12}$ is selected from the group consisting of hydrogen, halogen, cyano, nitro, and $X6S(=O)_jR_{32}$, wherein j is 2, and $R_{32}$ is selected from the group consisting of H and substituted or unsubstituted $C_{1-6}$ alkyl.

5. The compound according to claim 1, or a pharmaceutically acceptable salt thereof, wherein $R_4$ is selected from the group consisting of H, cyano, and substituted or unsubstituted $C_{1-6}$ alkyl.

6. The compound according to claim 1, or a pharmaceutically acceptable salt thereof, wherein the compound is selected from:

| Compound No. | Structure of compound |
|---|---|
| 7 | 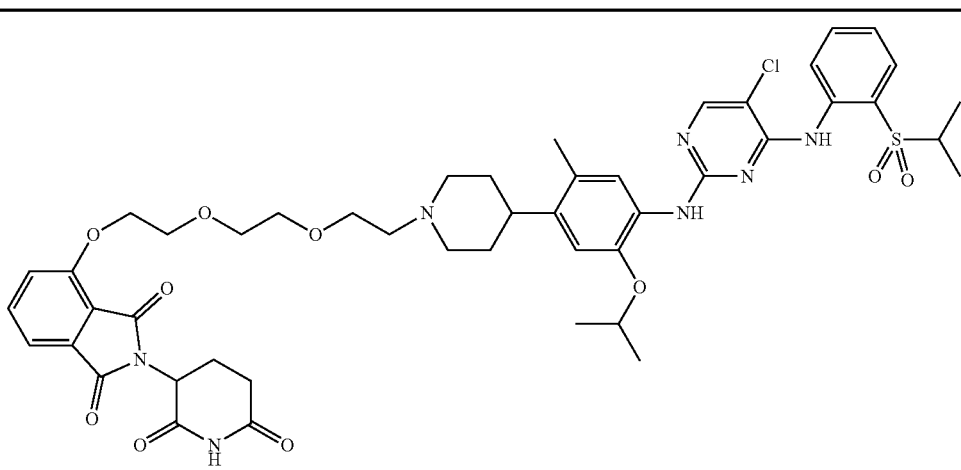 |

| Compound No. | Structure of compound |
|---|---|
| 10 | 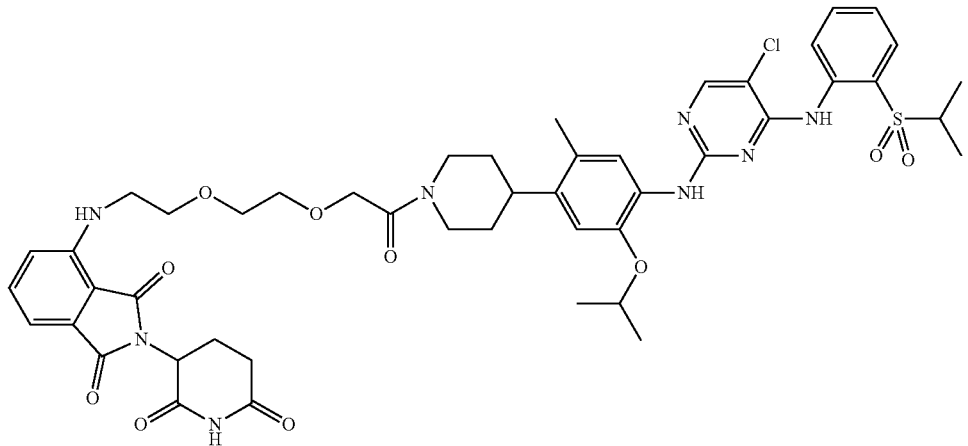 [SMILES: Cc1cc(Nc2ncc(Cl)c(Nc3ccccc3S(=O)(=O)C(C)C)n2)c(OC(C)C)cc1C1CCN(C(=O)COCCOCCNc2cccc3c2C(=O)N(C2CCC(=O)NC2=O)C3=O)CC1] |
| 14 | 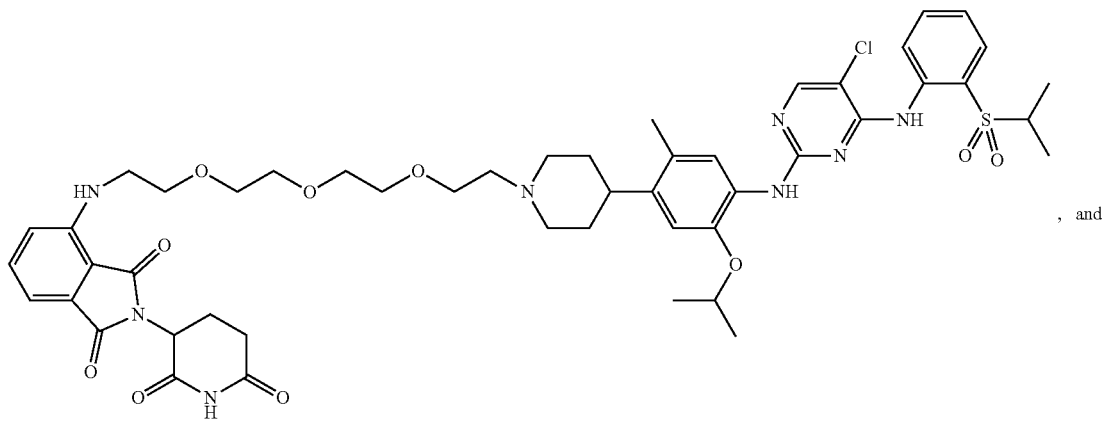 [SMILES: Cc1cc(Nc2ncc(Cl)c(Nc3ccccc3S(=O)(=O)C(C)C)n2)c(OC(C)C)cc1C1CCN(CCOCCOCCOCCNc2cccc3c2C(=O)N(C2CCC(=O)NC2=O)C3=O)CC1], and |
| 15 | 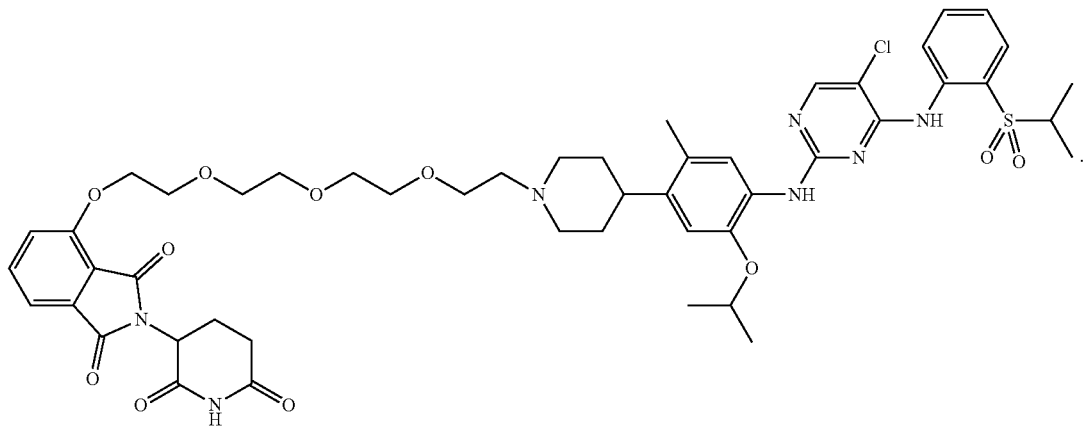 [SMILES: Cc1cc(Nc2ncc(Cl)c(Nc3ccccc3S(=O)(=O)C(C)C)n2)c(OC(C)C)cc1C1CCN(CCOCCOCCOCCOc2cccc3c2C(=O)N(C2CCC(=O)NC2=O)C3=O)CC1]. |

7. The compound according to claim 1, or a pharmaceutically acceptable salt thereof, wherein the compound is represented by formula I':

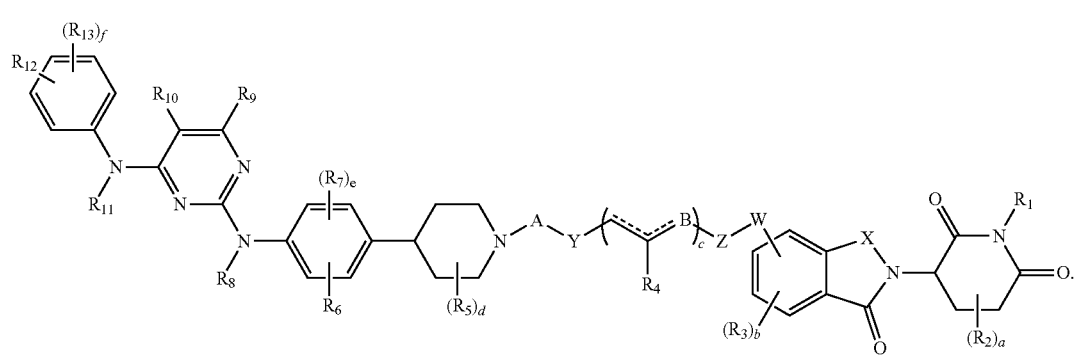

I'

8. The compound according to claim 1, or a pharmaceutically acceptable salt thereof, wherein the compound is represented by formula I":

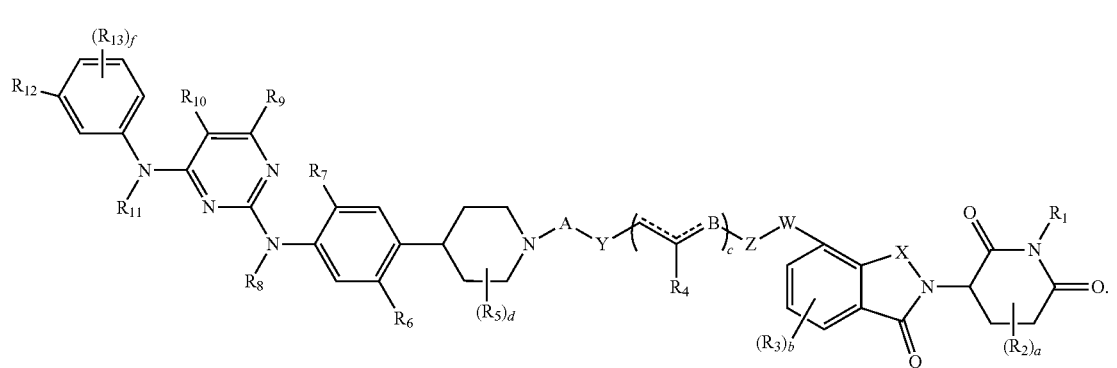

I"

9. A pharmaceutical composition, wherein the composition comprises the compound according to claim h or a pharmaceutically acceptable salt thereof, and a pharmaceutically acceptable carrier.

* * * * *